US010874685B2

(12) United States Patent
Jandaghi et al.

(10) Patent No.: US 10,874,685 B2
(45) Date of Patent: Dec. 29, 2020

(54) PANCREATIC CANCER THERAPY AND DIAGNOSIS

(71) Applicants: Deutsches Krebsforschungszentrum Stiftung des Öffentlichen Rechts, Heidelberg (DE); The Royal Institution for the Advancement of Learning/McGill University, Montreal (CA)

(72) Inventors: Pouria Jandaghi, Montreal (CA); Yasser Riaz Alhosseini, Montreal (CA); Daniel Scott Auld, Pointe-Claire (CA); Veena Sangwan, Montreal West (CA)

(73) Assignees: THE ROYAL INSTITUTION FOR THE ADVANCEMENT OF LEARNING/MCGILL UNIVERSITY, Montreal (CA); DEUTSCHES KREBSFORSCHUNGSZENTRUM STIFTUNG DES ÖFFENTLICHEN RECHTS, Heidelberg (DE)

( * ) Notice: Subject to any disclaimer, the term of this patent is extended or adjusted under 35 U.S.C. 154(b) by 0 days.

(21) Appl. No.: 16/538,139

(22) Filed: Aug. 12, 2019

(65) Prior Publication Data
US 2020/0030356 A1    Jan. 30, 2020

Related U.S. Application Data

(63) Continuation-in-part of application No. 15/304,598, filed as application No. PCT/EP2015/058380 on Apr. 17, 2015, now Pat. No. 10,420,757.

(30) Foreign Application Priority Data

Apr. 17, 2014    (EP) .................................... 14165053

(51) Int. Cl.
*A61K 31/7068*    (2006.01)
*A61P 35/00*    (2006.01)
*A61K 31/40*    (2006.01)
*G01N 33/574*    (2006.01)

(52) U.S. Cl.
CPC .......... *A61K 31/7068* (2013.01); *A61K 31/40* (2013.01); *A61P 35/00* (2018.01); *G01N 33/57438* (2013.01)

(58) Field of Classification Search
CPC ..... A61K 31/40; A61K 31/7068; A61P 35/00; G01N 33/57438
See application file for complete search history.

(56) References Cited

U.S. PATENT DOCUMENTS

| 8,445,517 B2 | 5/2013 | Frank |
| 9,283,192 B2 | 3/2016 | Mullen et al. |
| 10,420,757 B2 * | 9/2019 | Jandaghi ............ A61K 31/7068 |
| 2011/0144043 A1 | 6/2011 | Frank |

FOREIGN PATENT DOCUMENTS

| WO | WO 2004/103262 | 12/2004 |
| WO | WO 2009/049242 | 4/2009 |
| WO | WO 2009/070331 | 6/2009 |
| WO | WO 2012/116432 | 9/2012 |
| WO | WO 2013/143000 | 10/2013 |

OTHER PUBLICATIONS

An et al. "Anti-proliferative effects and cell death mediated by two isoforms of dopamine D2 receptors in pituitary tumor cells." Mol Cell Endocrinol. Aug. 29, 2003;206(1-2):49-62.
Coufal et al. "Increased local dopamine secretion has growth-promoting effects in cholangiocarcinoma", International Journal of Cancer, Jan. 1, 2009.
Gemignani et al "Polymorphisms of the dopamine receptor gene DRD2 and colorectal cancer risk.", Cancer Epidemiol Biomarkers Prev. Jul. 2005;14(7):1633-8.
International Search Report issued in Application No. PCT/EP2015/058380, dated Dec. 16, 2015.
Kim et al. "Haloperidol induces demethylation and expression of the dual specificity phosphatase 6 gene in MIA PaCa-2 human pancreatic cancer cells", Life Sciences, vol. 91, Nos. 25-26, Dec. 1, 2012, pp. 1317-1322.
Moore et al., "Erlotinib Plus Gemcitabine Compared with Gemcitabine Alone in Patients with Advanced Pancreatic Cancer: A Phase III Trial of the National Cancer Institute of Canada Clinical Trials Group," *Journal of Clinical Oncology*, 2007; 25(15): 1960-1966.
Senogles "D2 dopamine receptor-mediated antiproliferation in a small cell lung cancer cell line, NCI-H69." Anticancer Drugs. Aug. 2007;18(7):801-7.

* cited by examiner

*Primary Examiner* — Lawrence E Crane
(74) *Attorney, Agent, or Firm* — Norton Rose Fulbright US LLP

(57) ABSTRACT

The present disclosure provides a novel method for treating pancreatic cancer and pancreatitis in which a combination of a dopamine receptor antagonist (pimozide, haloperidol, and/or L-741,626), 2-deoxy-D-glucose and atorvastatin are used, optionally in combination with gemcitabine.

11 Claims, 12 Drawing Sheets

1A

Normal

1B

CP

1C

PDAC

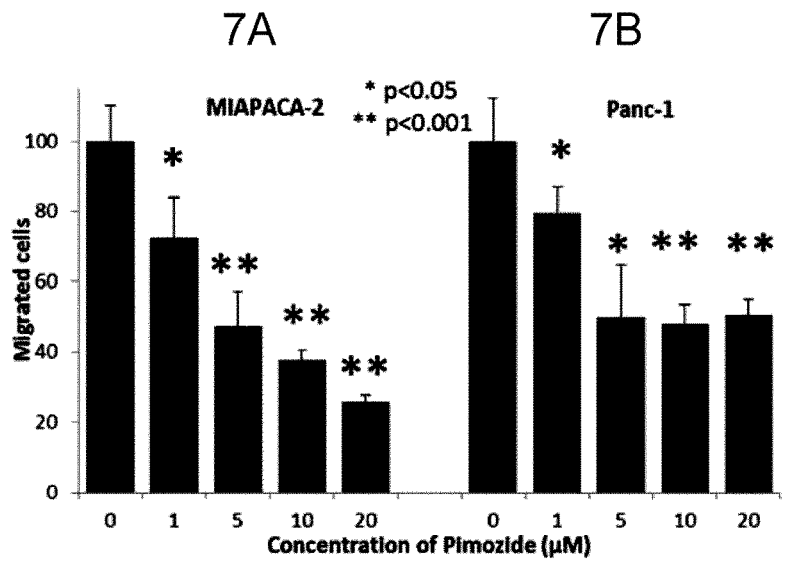
FIG. 7A-7B
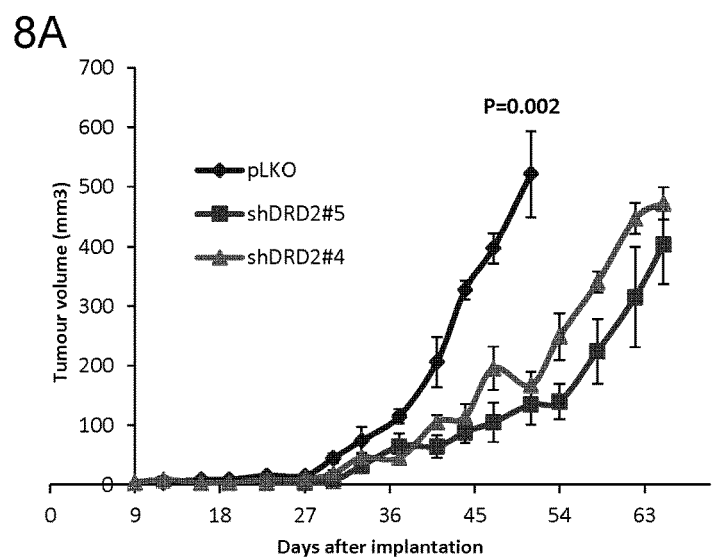
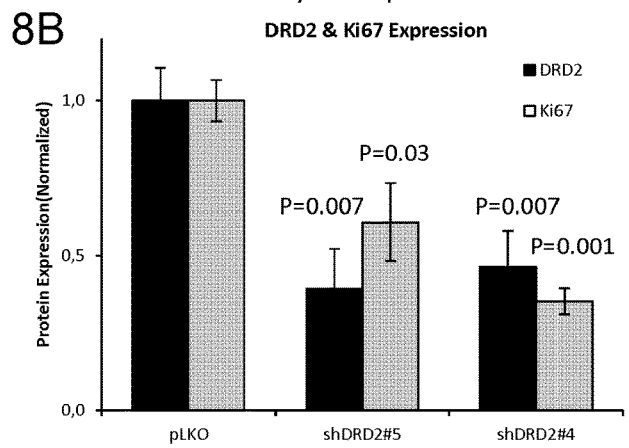
FIG. 8A-8B

PANCREATIC CANCER THERAPY AND DIAGNOSIS

CROSS-REFERENCE TO RELATED APPLICATIONS

This application is a continuation-in-part of co-pending U.S. patent application Ser. No. 15/304,598 filed 17 Oct. 2016, which is a national phase application under 35 U.S.C. § 371 of International Application No. PCT/EP2015/058380 filed 17 Apr. 2015, which claims priority to European Patent Application No. 14165053.1 filed 17 Apr. 2014. The entire contents of each of the above-referenced disclosures is specifically incorporated by reference herein without disclaimer.

FIELD OF THE DISCLOSURE

The present disclosure provides combinations for treating pancreatic cancer and pancreatitis. The combinations comprise antagonists of dopamine receptors that inhibit the growth of pancreatic cancer cells.

BACKGROUND

Pancreatic cancer has one of the highest mortality rates among all cancers and is the fourth most common cause of adult cancer death in the United States with an estimated 42,470 cases per year. About 3% of all newly diagnosed cancers are pancreatic cancers in the United States every year, with a 5 year survival rate of only 5%. The high mortality rate from pancreatic cancer is a result of the high incidence of metastatic disease at the time of diagnosis. As a result, only 5%-15% of patients are candidates for surgical resection in case of early stage diagnosis.

Pancreatic cancers can arise from both the exocrine and endocrine portions of the pancreas. Of pancreatic tumors, 95% develop from the exocrine portion of the pancreas, including the ductal epithelium, acinar cells, connective tissue, and lymphatic tissue. Approximately 75% of all pancreatic carcinomas occur within the head or neck of the pancreas, 15-20% occur in the body of the pancreas, and 5-10% occur in the tail.

Cancer recurrence can be local (in or near the same place it started) or distant (spread to organs such as the liver, lungs, or bone). When pancreatic exocrine cancer recurs, it is essentially treated the same way as metastatic cancer, and is likely to include chemotherapy if the patient can tolerate it. Typically, pancreatic cancer first metastasizes to regional lymph nodes, then to the liver, and, less commonly, to the lungs. It can also directly invade surrounding visceral organs such as the duodenum, stomach, and colon or metastasize to any surface in the abdominal cavity via peritoneal spread. Ascites may result, and this has an ominous prognosis. Pancreatic cancer may spread to the skin as painful nodular metastases. Pancreatic cancer uncommonly metastasizes to bone.

Five to ten percent of pancreatic cancer in patients is related to hereditary factors. Although the exact genetic ablation responsible for this condition has not been reported, an increased number of PDAC cases show association with inherited cancer syndromes. Another known cause of elevated pancreatic cancer risk is tobacco smoking that ranged between 3 and 1.5 times in current non-smokers and smokers respectively. Diabetes mellitus and chronic pancreatitis seem to have significant impact on the development of PDAC when compared with healthy populations.

Treatment of pancreatic cancer depends on the stage of the cancer. When the disease is confined to the pancreas and clearly separated from surrounding blood vessels (i.e. local and resectable), the treatment of choice is surgery with post-operative chemotherapy and/or radiation. When the disease encases or compresses surrounding blood vessels or has extended into adjacent structure, chemotherapy and/or radiation is proposed. In rare cases, when the patient responds well to treatment, the tumour may subsequently be surgically resected. When the disease is metastatic, chemotherapy is proposed. In most cases, these treatments do not represent a cure and the median survival ranges from 3 to 18 months depending on the stage of the disease. Each of these standard treatments is described in more detail below.

Surgical resection offers the only chance for a cure for pancreatic cancer. Approximately 20% of patients present with pancreatic cancer amenable to local surgical resection, with operative mortality rates of approximately 1 to 16%. Following surgery, median survival time is 14 months. For pancreatic cancer, the benefit of radiotherapy alone is unclear and radiotherapy is mostly used in conjunction with chemotherapy (referred to as chemoradiation). Chemotherapy may be used in patients with advanced unresectable cancer (locally advanced or metastatic) and in patients with localized disease after surgery or, sometime, beforehand in order to shrink the tumour. Gemcitabine, and to a lesser extent 5-fluorouracil (5-FU), are the chemotherapy drugs of choice to treat pancreatic cancer. Meta-analyses show that chemotherapy has significant survival benefits over best supportive care. Standard gemcitabine therapy for patients with locally advanced, unresectable, or metastatic pancreatic adenocarcinoma, provides a median overall survival (OS) of 6 months and 1-year survival rate of 21%.

Pancreatic cancer is one of the most aggressive types of common tumor and possesses multiple genetic abnormalities. This aggressive behavior of pancreatic cancer gives it the ability to obtain resistance to conventional treatment approaches such as radiation, surgery, chemotherapy or combination of them. Targeted treatments have shown successful treatment response to therapy in other solid tumors by examination of different specific small molecules which are known to be selective inhibitor against their target. This evidence supports the need for further investigation to find complementary therapy based on gene mutations or important pathways involved in the development of pancreatic cancer.

SUMMARY

The present disclosure concerns a method for the treatment of pancreatic cancer or pancreatitis in a subject in need thereof. The method comprises administering a therapeutically effective amount of a dopamine receptor antagonist, a glycolysis inhibitor, and a cholesterol lowering agent to the subject in need thereof. In an embodiment, the method further comprises administering a therapeutically effective amount of a chemotherapeutic agent. In still another embodiment, the dopamine receptor antagonist is a dopamine receptor D2 (DRD2) antagonist. In another embodiment, the DRD2 antagonist is an RNAi construct. In another embodiment, the DRD2 antagonist is an antibody. In still another embodiment, the DRD2 antagonist is a small molecule such as, for example, pimozide, haloperidol, and/or L-741,626. In a specific embodiment, the DRD2 antagonist is pimozide. In still another embodiment, the glycolysis inhibitor is an inhibitor of hexokinase, such as, for example, 2-deoxy-D-glucose (2-DG). In yet another embodiment, the cholesterol lowering agent is a 3-hydroxy-3-methylglutaryl coenzyme A (HMG-CoA) reductase inhibitor, such as, for example atorvastatin or a pharmaceutically acceptable salt thereof. In still a further embodiment, the chemotherapeutic agent is gemcitabine. In some embodiments, the pancreatic cancer is an adenocarcinoma, such as, for example, a pancreatic ductal adeno-carcinoma (PDAC). In other embodiments, the pancreatitis is a chronic pancreatitis. In some embodiments, the method further comprises determining the presence or absence of DRD2 in a biological sample obtained from the subject. In some embodiments, the subject is a human. In other embodiments, the dopamine receptor antagonist, the glycolysis inhibitor, and the cholesterol lowering agent are administered daily.

DESCRIPTION OF THE DRAWINGS

The present disclosure will now be further described in the following examples with reference to the accompanying figures and sequences, nevertheless, without being limited thereto. For the purposes of the present disclosure, all references as cited herein are incorporated by reference in their entireties. In the Figures:

FIGS. 7A and 7B show a dose dependent inhibitory effect of Pimozide on migration of PDAC cells using Boyden chamber. MIAPaCa-2 cells were platted on transwells and exposed to increasing doses of Pimozide for 4 h (FIG. 7A). Migrated cells were measured and normalized to their controls. Values are the mean+/−SD of four replicate. The Dose dependent inhibitory effect of Pimozide on PANC-1 cells migration was assessed as described above using Boyden chamber (FIG. 7B).

FIGS. 8A and 8B show an inhibition of tumor growth in vivo. Mice implanted with PANC-1 cell and expressing shDRD2 or control constructs were monitored for tumor growth (FIG. 8A). Relative protein expression of DRD2 and Ki67 in tumors collected from mice as measured by IHC (FIG. 8B).

Figure 12A:
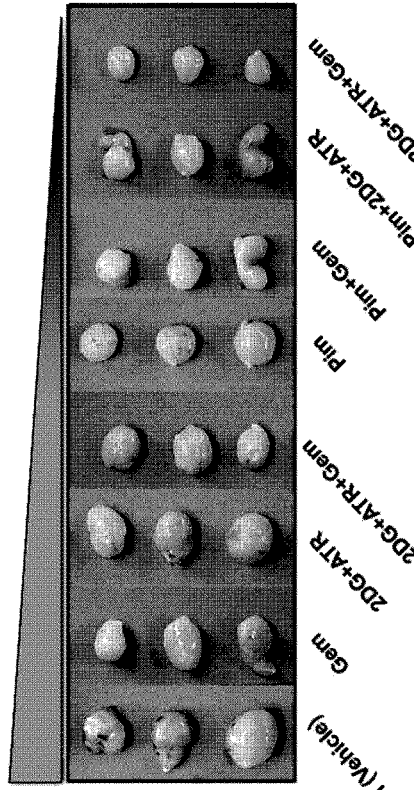
Figure 12B:
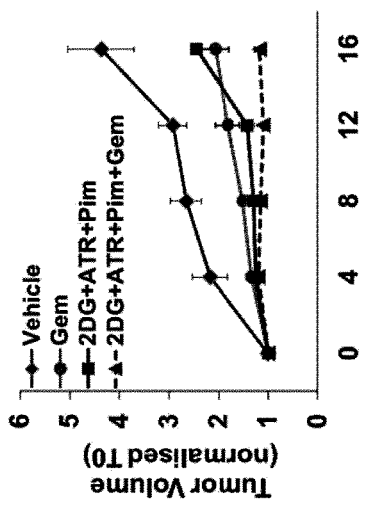

FIGS. 12A to 12D show that a treatment with combination of Gemcitabine, Pimozide, 2-DG and ATR stops tumor growth in vivo. Tumor volumes normalized to initial measurement shown in the y-axis every four days following treatment with either vehicle (gray line), the chemotherapeutic gemcitabine (green line), a combination therapy of 2-deoxy-D-glucose, atorvastatin and pimozide (2DG+ATR+Pim, redline), or a combination therapy of 2DG+ATR+Pim and gemcitabine (2DG+ATR+Pim+Gem, red dashed line) (FIG. 12A). Photographs of tumors harvested following the 16 day treatment protocol with, from left to right, control (Vehicle), gemcitabine (Gem) alone, 2DG+ATR, 2DG+ATR+Gem, Pim alone, Pim+Gem, Pim+2DG+ATR, or Pim+2DG+ATR+Gem (FIG. 12B). Tumor weight (FIG. 12C) and volume of samples (FIG. 12D) harvested following treatment with, from left to right, control (Vehicle), 2DG+ATR, Pim alone, Pim+2DG+ATR, Gem alone, 2DG+ATR+Gem, Pim+Gem, or Pim+2DG+ATR+Gem.

DETAILED DESCRIPTION

In view of the above described limited options for a successful treatment of pancreatic cancer in the art, providing new therapeutic combinations for pancreatic cancer targets are sought. Thus, one of the objective of the present disclosure is to provide a novel pancreatic cancer target, and in particular novel therapeutic strategies to treat or prevent pancreatic cancer and/or pancreatitis. Another object of the disclosure intends to provide alternative diagnostic methods that allow diagnosing the occurrence of pancreatic cancer in a subject, or at least help to establish a pancreas cancer diagnosis. The therapeutic combinations of the present disclosure include a dopamine receptor antagonist, a glycolysis inhibitor and a cholesterol lowering agent. The therapeutic combination of the present disclosure can optionally include a chemotherapeutic agent.

The term "chronic pancreatitis" refers to a condition of the pancreas characterized by a long-standing inflammation of the pancreas that alters the organ's normal structure and functions. It can present as episodes of acute inflammation in a previously injured pancreas, or as chronic damage with persistent pain or malabsorption. Chronic pancreatitis is known to be a risk factor for the development of pancreatic cancers.

The term "cancer" as referred to in the present disclosure relates to any neoplastic disease which is characterized by abnormal and uncontrolled cell division causing malignant growth or tumor. Cancer cells, unlike benign tumor cells, exhibit the properties of invasion and metastasis and are highly anaplastic. In some embodiments, said cancer is a solid tumor (i.e. essentially solid neoplasmic growth, with low liquid content that is other than a cyst) or tumor metastasis (i.e. at its metastatic stage of disease).

The term "treatment of cancer", or "treatment of pancreatic cancer" as used in the context of the present disclosure relates to any kind of change in the disease state or condition of a subject in need thereof including any degree of: a decrease in tumor size; decrease in rate of tumor growth; stasis of tumor size; decrease in the number of metastasis; decrease in the number of additional metastasis; decrease in invasiveness of the cancer; decrease in the rate of progression of the tumor from one stage to the next, inhibition of tumor growth in a tissue of a mammal having a malignant cancer, control of establishment of metastases, inhibition of tumor metastases formation, regression of established tumors as well as decrease in the angiogenesis induced by the cancer. The term "treatment of cancer" can also refer to prophylactic treatment, such for example the prevention of cancer reoccurs after previous treatment (including surgical removal) and prevention of cancer in an individual prone (genetically, due to life style, chronic inflammation and so forth) to develop cancer.

The term "administering" or its other lingual forms as used in the context of the present disclosure relates to the path by which a pharmaceutically active component, a drug, fluid or other substance is brought into contact with the body of a subject. The pharmaceutical composition is transported from the site of entry to the part of the body where its action is desired to take place, According to one embodiment of the present disclosure, said administering may be achieved via any medically acceptable means suitable for a pharmaceutical composition of the disclosure or any component thereof, including oral, rectal, vaginal, nasal, topical, transdermal, or parenteral (including subcutaneous, intramuscular, intrasynovial, intraperitoneal, intradermal and intravenous) administration.

In therapeutic applications, the dosages and administration schedule of components of a pharmaceutical composition of the disclosure may vary depending on the component, the age, weight, sex and clinical condition of the recipient patient, and the experience and judgment of the clinician or practitioner administering the therapy, among other factors affecting the selected dosage. Generally, the dose and administration scheduled should be sufficient to result in slowing and/or regressing, the growth of the tumor (s) and may also cause complete regression of the cancer. In some cases, regression may be monitored via direct imaging (e.g. MRI) or by a decrease in blood levels of tumor specific markers. An effective amount of the pharmaceutical composition is that which provides a medical benefit as noted by the clinician or other qualified observer. Regression of a tumor in a patient is typically measured with reference to the diameter of a tumor. Decrease in the diameter of a tumor indicates regression. Complete regression is also indicated by failure of tumors to reoccur after treatment has stopped. The present disclosure allows for the administration of a pharmaceutical composition of the present disclosure, either prophylactically or therapeutically or in the context of adjuvant or neo-adjuvant treatment.

When provided prophylactically, antagonists, combinations or compositions of the disclosure may be administered in advance of any symptom. Prophylactic administration of pharmaceutical compositions may serve to prevent or inhibit cancer or chronic pancreatitis. A pharmaceutical composition of the disclosure may prophylactically be administered to a patient with, for example, a family history of pancreatic cancer or chronic pancreatitis. The risk for developing pancreatic cancer or chronic pancreatitis may be determined by measuring levels of pancreatic cancer or chronic pancreatitis marker proteins in a biological sample (for example a pancreatic tissue sample of a patient) or by genetic markers (such as, for example DRD2).

Therefore in one embodiment of the disclosure said treatment of pancreatic cancer or pancreatitis comprises the administration of said antagonist to a subject suffering from pancreatic cancer or chronic pancreatitis. Preferably a therapeutically sufficient amount of said antagonist is administered to said subject.

The term "subject" in context of the disclosure preferably refers to a mammal, preferably a human.

Other preferred embodiments of the disclosure pertain to pancreatic cancer which is primary pancreatic cancer, metastatic pancreatic cancer, refractory pancreatic cancer, recurrent pancreatic cancer, and/or cancer drug resistant pancreatic cancer. A pancreatic cancer of the disclosure may be an adenocarcinoma, preferably ductal adenocarcinoma.

Preferred alternative embodiments for all aspects of the disclosure pertain to only pancreatic cancer, and not chronic pancreatitis.

Dopamine Receptor Antagonists

Dopamine receptors are G protein-coupled receptors that are prominent in the vertebrate central nervous system (CNS). The neurotransmitter dopamine is the primary endogenous ligand for dopamine receptors. Dopamine receptors are implicated in many neurological processes, including motivation, pleasure, cognition, memory, learning, and fine motor control, as well as modulation of neuroendocrine signalling. Abnormal dopamine receptor signalling and dopaminergic nerve function is implicated in several neuropsychiatric disorders. Thus, antipsychotics are often dopamine receptor antagonists while psychostimulants are typically indirect agonists of dopamine receptors.

Pharmacological and molecular biological studies have shown that the dopamine receptor family can be divided into five subclasses D1-5. The best characterized of these are D1 and D2 families. The dopamine receptor D2 (DRD2) subtype exists in a long and short form, the long form having a larger intracellular loop than the short form. These receptor subtypes appear to be anatomically, biochemically and behaviourally distinct. D1 and D2 receptors are reported to have opposite biochemical effects on adenylate cyclase activity, and stimulation of D1 and D2 receptors produces different behavioural responses. The dopamine receptor subtypes can be separately and independently modulated through the administration of selective agonists and antagonists.

Pimozide for example is a DRD2 antagonist having the chemical structure of formula.

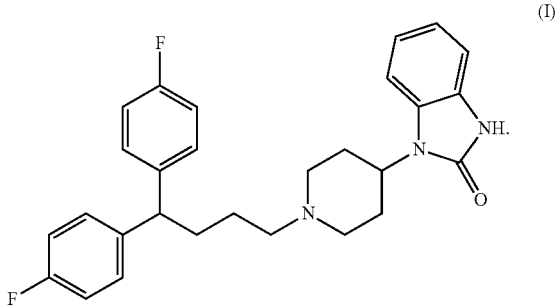 [SMILES: O=c1[nH]c2ccccc2n1C1CCN(CCCC(c2ccc(F)cc2)c2ccc(F)cc2)CC1]

(I)

Pimozide is an FDA approved drug and used in its oral preparation in schizophrenia and chronic psychosis, Tourette syndrome and resistant tics. Pimozide has been used in the treatment of delusional disorder and paranoid personality disorder. It has also been used for delusions of parasitosis. Also many other dopamine receptor antagonists and agonists are known in the art.

WO 2012/116432 observes the use of modulators of dopamine receptor function or expression in the treatment of leukaemia. WO 2012/116432 discloses anti proliferative effects of dopamine receptor antagonists against acute myeloid leukaemia. The use of dopamine receptor antagonists for treating other malignancies is not supported.

WO 2013/143000 provides combinations of the multi dopamine receptor antagonist thioridazine and the leukemic therapeutic cytarabizine as beneficial in the therapy of acute myeloid leukemia. The document in particular emphasises the beneficial use against leukaemia of drugs that target multiple dopamine receptors at the same time, such as thioridazine.

In addition, the expression of dopamine receptors in various malignancies is highly controversially discussed. Melanoma cells for example do not appear to express the dopamine D2 receptor, which was shown by Boeni R, et al. (Dermatology. 1996). For DRD2, it is even known that reduced expression of the receptor is associated with the occurrence of colorectal cancer (Gemignani F et al: "Polymorphisms of the dopamine receptor gene DRD2 and colorectal cancer risk.", Cancer Epidemiol Biomarkers Prev. 2005 July; 14(7):1633-8).

Other studies revealed that supporting expression and activity of dopamine receptors, in particular of DRD2, is beneficial in the treatment of small cell lung cancer (Senogles S: "D2 dopamine receptor-mediated antiproliferation in a small cell lung cancer cell line, NCI-H69." Anticancer Drugs. 2007 August; 18(7):801-7). DRD2 agonists were shown to be applicable in cancer treatments. After either dopamine or quinpirole (DRD2 agonist) treatment, the cancer cell viability decreased significantly (An J J et al.: "Anti-proliferative effects and cell death mediated by two isoforms of dopamine D2 receptors in pituitary tumor cells." Mol Cell Endocrinol. 2003 Aug. 29; 206(1-2):49-62).

In context of the present disclosure, it was found that the dopamine receptor DRD2 is significantly expressed in chronic pancreatitis as a strong risk factor for pancreatic cancer and tumor cells of the pancreatic ductus. This is in view of the mixed reports regarding the expression of dopamine receptors in several malignancies very surprising—indeed dopamine receptors in pancreatic cancers provide in accordance with the present disclosure a promising new pancreatic cancer target for the development of new treatment regimens which will be described in more detail herein below. More importantly, it was observed that inhibiting the expression of DRD2 using a shRNA construct induced cell death specifically in cancer cells. This effect could be reproduced using exemplary small molecular antagonists of DRD2, namely pimozide, haloperidol or L-741,626. Pimozide has a high affinity to DRD2 and blocks the protein's function efficiently. L-741,626 is a very selective inhibitor of DRD2, and also blocks efficiently DRD2 activity. Haloperidol is another dopamine receptor D2 antagonist. Thus, the present disclosure provides proof that inhibition of dopamine receptors in the pancreas at various levels, both protein expression, and inhibition of the activity of expressed protein, is beneficial for a pancreatic cancer treatment. Both inhibition of the expression and the activity of DRD2 yielded into a significant toxic effect in cancer cells. Moreover, cell-growth inhibitory function of DRD2 antagonist on pancreatic cancer cells is considerably stronger than on normal fibroblast cells. These results are in agreement with the herein disclosed observations that protein levels of DRD2 are different when comparing pancreatic ductal cancer versus normal ductal pancreas tissue in this study. Therefore, the disclosure provides a teaching that various kinds of dopamine receptor antagonists, in particular antagonists of DRD2, can be applied in the therapy of a patient suffering from a pancreatic cancer or pancreatitis. Since pancreatitis and specifically chronic pancreatitis (CP) is known to be a condition observed in advance of cancer development in the pancreas, the compounds and methods of the disclosure can equally be used for pancreatitis and preferably chronic pancreatitis.

The term "antagonist of a dopamine receptor" refers to a compound that produces any detectable or measurable reduction in the expression, function or activity of one or more dopamine receptors. The terms "antagonist" and "inhibitor" shall be used interchangeably herein. In one embodiment, the dopamine receptors (DR) are selected from DRD1, DRD2, DRD3, DRD4 and DRD5, however, in the context of the present disclosure antagonists of DRD2 are preferred. Whether or not a candidate compound or molecule qualifies as an antagonist of a dopamine receptor in accordance to the disclosure can be easily assessed by the skilled person using standard procedures in the art, for example by measuring dopamine receptor enzymatic activity, or using dopamine receptor specific reporter assays in cell culture models. Expression of dopamine receptor can be assessed by quantitative RT-PCR or immunohistochemically, using antibodies against the respective dopamine receptor. DRD2 antibodies are for example available from Santa Cruz Biotechnology® (Cat No. sc-5303). In order to assess the activity or function of DRD2, one possibility is to use DRD2 ligand binding assays, that are well known in the art and qualify for high throughput approaches (for example as presented by Mathias G et al. SBS 17th Annual Conference, April 2011, Orlando, USA).

In certain embodiments of the disclosure the antagonist of a dopamine receptor is selected from the group consisting of an RNAi construct, an antibody and a small molecule.

An RNAi (RNA interference) construct usually comprises a nucleotide sequence that is complementary to the nucleotide sequence of the mRNA of a dopamine receptor. Such RNAi constructs are well known in the art and can be provided as short hairpin RNAs (shRNA) or small interfering RNAs (siRNA).

Preferred RNAi constructs in accordance with the disclosure are lentiviral shRNA targeting DRD2, preferably which can be found at http://www.sigmaaldrich.com/life-science/functional-genomics-and-rnai/shrna/library-information-.html or http://www.broad.mit.edu/genome_bio/trc/rnai.html. Most preferred are the vectors TRCN0000011342 and TRCN0000011343.

"RNA interference" refers to sequence-specific, post-transcriptional gene silencing of a selected target gene. The RNAi agents in the context of the present disclosure, preferably, reduce the expression of a dopamine receptor, or a dopamine receptor signalling gene by degradation of RNA transcribed from said dopamine receptor signalling gene (target RNA) or by inhibition of translation of said target RNA. Target RNAs preferably are mRNAs coding for dopamine receptor signalling components, however, any type of RNA is encompassed by the RNAi methods of the disclosure. It is to be understood that silencing as used herein does not necessarily mean the complete abolishment of gene expression in all cases. RNAi, preferably, reduces gene expression by at least 50%, at least 60%, at least 70%, at least 80%, at least 90%, at least 95%, at least 98%, or at least 99% as compared to the expression level in a reference without RNAi.

RNAi requires in the cell the presence of double stranded RNAs (dsRNAs) that are homologous in sequence to the target RNAs. The term "dsRNA" refers to RNA having a duplex structure comprising two complementary and antiparallel nucleic acid strands. The RNA strands forming the dsRNA may have the same or a different number of nucleotides, whereby one of the strands of the dsRNA can be the target RNA. It is, however, also contemplated by the present disclosure that the dsRNA is formed between two sequence stretches on the same RNA molecule.

RNAi may be used to specifically inhibit expression of dopamine receptor, or dopamine receptor signalling genes of the present disclosure in vivo. Accordingly, it may be used for therapeutic approaches to treat pancreatic cancers which are accompanied with an altered expression of at least one of the dopamine receptor signaling genes of the present disclosure. For such therapeutic approaches, expression constructs for siRNA or shRNA may be introduced into target cells of the host which suffer from dopamine receptor gene expression. Accordingly, siRNA may be combined efficiently with other therapy approaches.

Methods relating to the use of RNAi to silence genes in animals, including mammals, are known in the art (see, for example, Hammond et al. (2001), Nature Rev. Genet. 2, 110-119; Bernstein et al. (2001), Nature 409, 363-366; WO 9932619; and Elbashir et al. (2001), Nature 411: 494-498).

As used herein, the term "RNAi construct", preferably, refers to a shRNA, siRNA or a miRNA construct as specified herein. The RNAi construct of the present disclosure is of sufficient length and complementarity to stably interact with the target RNA, i.e. it comprises at least 15, at least 17, at least 19, at least 21, at least 22 nucleotides complementary to the target RNA. By "stably interact" is meant interaction of the RNAi construct or its products produced by the cell with a target RNA, e.g., by forming hydrogen bonds with complementary nucleotides in the target RNA under physiological conditions.

Small molecule DRD antagonists of the disclosure include, but are not limited to acetopromazine maleate salt, acetophenazine (D2 receptor antagonist), alizapride (D2 receptor antagonist), amisulpride (D2 and D3 receptor antagonist), aripiprazole (D2 and 5-HT2A receptor antagonist; also known as ABILIFY® and ABILIFY MYCITE®), aripiprazole lauroxil (also known as ARISTADA® and Aristada Initio™), asenapine (D2 and 5-HT2A receptor antagonist) (also known as SAPHRIS®), azaperone, benperidol (dopamine antagonist), benzo[a]phenanthridine-10, 11-diol, 5,6,6a,7,8,12b-hexahydro-, trans-[CAS] (D1 ligand), blonanserin (D2, D3, and 5-HT2A receptor antagonist), brexpiprazole (D2 and 5-HT1A receptor agonist; 5-HT2A, α1B, and α2C receptor antagonist) (also known as REXULTI®), buspirone (D2 receptor antagonist, 5-HT1A receptor partial agonist) (also known as BUSPAR®), bromopride (dopamine antagonist), bromperidol (dopamine antagonist), cariprazine (D2, D3, and 5-HT1A receptor agonist; 5-HT2A, 5-HT2B, Histamine H1 receptor antagonists; also known as VRAYLAR®), carphenazine (D1A, D1B, and D2 receptor antagonist), chlorpromazine hydrochloride (D2 antagonist; also known as THORAZINE®), chlorprothixene (D1A, D2, D3, 5-HT2A, 5-HT2B, 5-HT-2C receptor antagonist), clomipramine hydrochloride (chlorpromazine derivative), clozapine (D2 and 5-HT2A receptor antagonist; also known as CLOZARIL®, FAZACLO®, or VERSACLOZ®), dihydroergocristine (dopamine, serotonin, α- and β-adrenergic receptor antagonists), disulfiram (dopamine beta-hydroxylase inhibitor), DO 897/99 (D3 antagonist), domperidone (dopamine antagonists; also known as MOTILINUM®), droperidol (D2 (dopamine receptor) antagonist; also known as INAPSINE®), ethopropazine hydrochloride (thioridazine derivative), fluperlapine (DRD2 antagonist), fluphenazine dihydrochloride (DRD1 and DRD2 antagonist; also known as PROLIZIN®), fluspirilene (DRD2 antagonist), haloperidol (DRD2 antagonist; also known as HALDOL® and HALDOL® Decanoate), hydrastinine hydrochloride (dopamine receptor blocker), iloperidone (D2 and 5-HT2A receptor antagonist; also known as FANAPT®), indatraline (potent D antagonist), itopride (DRD2 antagonist and ACE inhibitor), JNJ-37822681 (DRD2 antagonist), levosulpiride (D2, D3, and D4 receptor antagonist), loxapine succinate (DRD2 and DRD4 antagonist; also known as LOXITANE® and ADASUVE®), lurasidone (DRD2 and 5-HT2A receptor antagonist; also known as LATUDA®), melperone (D2 receptor antagonist), mesoridazine (D2 antagonist), mesoridazine besylate (D antagonist; also known as SERENTIL®), methotrimeprazine maleat salt (thioridazine derivative), metixene hydrochloride (thioridazine derivative), metoclopramide (D2 receptor antagonist and M1 acetylcholine receptor; also known as REGLAN®, METOZOLV ODT®, or Reglan ODT™), molindone hydrochloride; also known as MOBAN®), nafadotride (D3 antagonist), olanzapine (DRD1 and DRD2 antagonist; also known as ZYPREXA®, ZYPREXA ZYDIS®, or ZYPREXA RELPREVV®), ONC201 (D2 receptor antagonist; also known as TIC10), paliperidone (D2, D3, D4, 5-HT2A, 5-HT2C receptor antagonist; also known as INVEGA®, INVEGA SUSTENNA®, or INVEGA TRINZA®), perospirone (DRD2 and DRD4 antagonist), perphenazine (DRD1 and DRD2 antagonist), phenothiazine (thioridazine derivative), pimozide (dopamine antagonist; also known as ORAP®), piperacetazine (thioridazine derivative), pipotiazine (DRD1A, DRD2, 5-HT1A, and 5-HT2A receptor antagonist), prochlorperazine (thioridazine derivative; also known as COMPRO® and COMPAZINE®), prochlorperazine dimaleate (dopamine antagonist), promazine hydrochloride, promethazine hydrochloride (thioridazine derivative), quetiapine (dopamine and serotonin receptors antagonist; also known as SEROQUEL® and SEROQUEL XR®), quetiapine (D2 antagonist), R(+)-SCH-23390 (D1 antagonist), raclopride (D2 antagonist), remoxipride, risperidone (DRD1 and DRD2 antagonist; also known as Perseris™ RISPERDAL®, and RISPERDAL® CONSTA®), S(−) Eticlopride hydrochloride, sertindole (DRD2/Serotonin, 5-HT2 receptor antagonist), SKF 83566 (D1 antagonist), spiperone (D2 antagonist), sulpiride (D2 antagonist), sulpiride (DRD2 and DRD3 antagonist), thiethylperazine malate (thioridazine derivative), thioproperazine dimesylate (DRD1 and DRD2 antagonist), thioridazine hydrochloride (thioridazine derivative; also known as MELLARIL®), thiothixene (DRD1A, DRD2, 5-HT2A receptor antagonist; also known as NAVANE®), trifluoperazine (DRD2 antagonist; also known as STELAZINE®), triflupromazine hydrochloride (DRD1 and DRD2 antagonist), trimeprazine tartrate (thioridazine derivative), trimethobenzamide hydrochloride (DRD2 antagonist), ziprasidone hydrochloride (DRD2/serotonin 5-HT2 antagonist; also known as GEODON®), zotepine (dopamine D2/serotonin 5-HT2 antagonist) and zuclopenthixol (D1A, D1B, and D2 receptor antagonist).

Particular preferred antagonists of the disclosure are selected from the group consisting of pimozide and L-741, 626, and preferably is pimozide. Other antagonists of the disclosure may be selected from the group consisting of Aceprometazine, Ecopipam, EEDQ, FLB 457, Flupenthixol decanoate, Hydroxyzine, Iodobenzamide, Levomepromazine, Tiapride, and Tiapride Hydrochloride.

The DRD antagonists can be provided as a pharmaceutically acceptable salt. The expression "pharmaceutically acceptable salt" refers to conventional acid-addition salts or base-addition salts that retain the biological effectiveness and properties of the compounds of formula (1) and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as e.g., tetramethylammonium hydroxide. The chemical modification of a pharmaceutical compound (i.e. drug) into a salt is a well-known technique which is used in attempting to improve properties involving physical or chemical stability, e.g., hygroscopicity, flowability or solubility of compounds.

The term "antibody" as used in this specification refers to a molecule from the subgroup of gamma globulin proteins which is also referred to as the immunoglobulins (Ig). Antibodies can, preferably, be of any subtype, i.e. IgA, IgD, IgE, IgM or, more preferably, IgG. Antibodies against dopamine receptor polypeptides of the disclosure can be prepared by well-known methods using a purified polypeptide or a suitable fragment derived therefrom as an antigen. A fragment which is suitable as an antigen may be identified by antigenicity determining algorithms well known in the art. Such fragments may be obtained either by proteolytic digestion from dopamine receptor polypeptides or may be synthetic peptides. Preferably, the antibody of the present disclosure is a monoclonal antibody, a polyclonal antibody, a single chain antibody, a human or humanized antibody or primatized, chimerized or fragment thereof. Also comprised as antibodies of the present disclosure are a bispecific or a trispecific antibody, a synthetic antibody, an antibody fragment, such as Fab, Fv or say fragments etc., or a chemically modified derivative of any of these. An antibody of the present disclosure preferably binds specifically (i.e. does not cross react with other polypeptides or peptides) to one dopamine receptor, preferably DRD2. Specific binding can be tested by various well known techniques.

The term "inhibitory antibody" relates to an antibody inhibiting the activity of a dopamine receptor referred to in accordance with the present disclosure. Said inhibition preferably is caused by binding of the inhibitory antibody to an active centre or to an interaction site of a dopamine receptor of the disclosure, causing an inhibition of dopamine receptor signalling in the cell treated with said inhibitory antibody. It is to be understood that inhibiting as used herein does not necessarily mean the complete abolishment of activity in all cases Inhibitory antibodies, preferably, reduce dopamine receptor signalling by at least 10%, at least 20%, at least 30%, at least 40%, or at least 50% as compared to a reference.

Preferred embodiments of the disclosure pertain to pimozide for use in the treatment of pancreatic cancer or chronic pancreatitis. In this regard said treatment with pimozide comprises an administration of pimozide in about 0.01 to 10 mg/kg body weight/day, preferably 0.1 to 0.5 mg/kg body weight/day, most preferably in about 0.2 mg/kg body weight/day.

Surprisingly it was found that the inhibition of dopamine receptors, such as DRD2, not only inhibited the tumor cell viability, but also had a significant impact—a reduction—on the migration capacity of tumor cells. Therefore, the antagonists of dopamine receptors in accordance with the present disclosure are useful for the specific treatment of metastatic tumors, or for the prevention of the development of pancreatic cancer metastasis.

As already disclosed before, the antagonist in accordance with the disclosure may be an inhibitor of the activity of said dopamine receptor, or an inhibitor of the expression of said dopamine receptor.

In another aspect the above problem is solved by providing a combination for use in the treatment of pancreatic cancer or chronic pancreatitis, comprising an antagonist of a dopamine receptor as described above, together with at least one additional anti-cancer drug. Such additional anti-cancer drug can include, without limitation, a glycolysis inhibitor and a cholesterol lowering agent.

Glycolysis Inhibitor

As indicated in the present disclosure, DRD antagonists increase glucose uptake in pancreatic cells and suppressing glucose uptake/metabolism reduced pancreatic cell growth as well as tumor growth. As such, combining a DRD antagonist with a glycolysis inhibitor can be useful in the treatment of pancreatic cancer or pancreatitis.

The glycolysis inhibitor prevents the metabolic use of glucose either directly by inhibiting enzymes involved in the glycolytic pathway or indirectly by preventing glucose uptake by the cell through glucose transporters, or indirectly by downregulating genes responsible for the uptake and metabolic breakdown of glucose.

In an embodiment, the glycolysis inhibitor is an insulin receptor antagonist which prevents or reduces the glucose uptake by the cancer cells. In still another embodiment, the glycolysis inhibitor is a therapeutic acid capable of reducing blood glucose.

In a specific embodiment, the glycolysis inhibitor is an inhibitor of 6-phosphofructo-2-kinase/fructose-2,6-bisphosphatase 3 (PFKFB3). The preferred inhibitor being, but not limited to, 3PO (aka (2E)-3-(3-pyridinyl)-1-(4-pyridinyl)-2-propen-1-one), PFK15 (aka 1-(4-Pyridinyl)-3-(2-quinolinyl)-2-propen-1-one), YN1 (aka 7,8-dihydroxy-3-(4-hydroxyphenyl)-4H-1-benzopyran-4-one), and YZ9 (aka 3-carbethoxy-7-hydroxycoumarin; or 7-hydroxy-2-oxo-2H-1-benzopyran-3-carboxylic acid ethyl ester).

In another embodiment, the glycolysis inhibitor targets hexokinase (HK) or hexokinase II (HK2) either by directly inhibiting the enzyme or indirectly dissociating the enzyme from its substrate. Direct inhibitors of HK include, but are not limited to, 2-deoxy-D-glucose (aka 2-DG; 2-deoxyglucose; 2-Deoxy-D-arabino-hexose; 2-deoxy-D-glucose; D-arabino-2-desoxyhexose; BA 2758; BA-2758; or NSC-15193) and ionidamine (aka 1-(2,4-dichlorbenzyl)-indazole-3-carboxylic acid; DICA; diclondazolic acid). In another embodiment, indirect glycolysis inhibitors include, but are not limited to, imatinib (aka α-(4-methyl-1-piperazinyl)-3'-((4-(3-pyridyl)-2-pyrimidinyl)amino)-p-toluidide; CGP-57148B; Imatinib mesylate; GLEEVEC®; Glivec; Apo-imatinib; Imatinib Accord; Imatinib Actavis; or Imatinib Teva) which inhibits the tyrosine kinase Bcr-Abl to decrease HK activity. Direct inhibitors of HK2 include, but are not limited to 3-bromopyruvate (aka bromopyruvic acid; 3-BrPA, bromopyruvate; or 3-bromo-2-oxopropionic acid), astraglin (aka 3,4',5,7-tetrahydroxyflavone 3-glucoside; 3-(β-D-glucopyranosyloxy)-5,7-dihydroxy-2-(4-methoxyphenyl)-4H-1-benzopyran-4-one; 3-glucosylkaempferol; kaempferol 3-β-D-glucopyranoside; or kaempferol 3-glucoside), benserazide (aka benserazide hydrochloride; or DL-serine 2-(2,3,4-trihydroxybenzyl) hydrazide hydrochloride), chrysin (aka 5,7-dihydroxyflavone), methyl jasmonate (aka methyl cis-jasmonate; (−)-methyl jasmonate; or methyl (−)-jasmonate), and resveratrol (aka (E)-5-(2-(4-hydroxyphenyl)ethenyl)-1,3-benzenediol(E)-5-(2-(4-hydroxyphenyl)ethenyl)-1,3-benzenediol; (E)-resveratrol; 3,4',5-trihydroxy-trans-stilbene; 3,4',5-trihydroxystilbene; and 3,5,4'-trihydroxystilbene; 5-[(E)-2-(4-hydroxyphenyl)vinyl]benzene-1,3-diol; trans-resveratrol).

In a specific embodiment, the glycolysis inhibitor blocks glucose-6-phosphate dehydrogenase (G6PD), 6-phosphogluconate dehydrogenase (6-PGD), or glyceraldehyde-3-phosphate dehydrogenase (GAPDH) or a combination thereof. The preferred G6PD and 6-PGD inhibitor being 6-AN (aka 6-aminonicotinamide; 6-Aminopyridine-3-carboxamide). The preferred GAPDH inhibitors being, but not exclusively, arsenic and heptelidic acid (aka koningic acid).

In an additional embodiment, glycolysis in inhibited by ablating the uptake of glucose across the plasma membrane by glucose transporters (GLUT), including but not limited to, GLUT1. The preferred GLUT inhibitor being, but not limited to, 3PO, epigallocatechin gallate (aka (−)-cis-2-(3,4,5-trihydroxyphenyl)-3,4-dihydro-1(2H)-benzopyran-3,5,7-triol 3-gallate; (−)-cis-3,3',4',5,5',7-hexahydroxy-flavane-3-gallate; EGCG; NVP-XAA 723; PF-EGCG 90; or antiscar), fasentin (aka N-[4-chloro-3-(trifluoromethyl)phenyl]-3-oxobutanamide), forskolin (aka 7β-acetoxy-8,13-epoxy-1α,6β,9α-trihydroxylabd-14-en-11-one; coleonolk; HL-362; L-75-1362B; NSC-357088; NSC-375489; colforsin; or coleonol), phloretin (aka β-(4-hydroxyphenyl)-2,4,6-dihydroxypropiophenone; 2',4',6'-trihydroxy-3-(4-hydroxyphenyl) propiophenone; or 3-(4-Hydroxyphenyl)-1-(2,4,6-trihydroxyphenyl)-1-propanone), quercetin (aka QUE; 2-(3,4-dihydroxyphenyl)-3,5,7-trihydroxy-4H-1-benzopyran-4-one; 3,3',4',5,7-pentahydroxyflavone; 3,5,7,3',4'-pentahydroxyflavone; sophoretin; xanthaurine; LDN-0052529; NSC-57655; or NSC-9219), STF31 (aka 4-[[[[4-(1,1-Dimethylethyl)phenyl]sulfonyl]amino]methyl]-N-3-pyridinyl-benzamide), WZB117 (aka WZB-117; 3-fluoro-1,2-phenylene bis(3-hydroxybenzoate); and 3-hydroxy-benzoic acid 1,1'-(3-fluoro-1,2-phenylene) ester). The preferred GLUT1 selective inhibitor being, but not exclusively, cytochalasin B (aka phomin).

In another embodiment, glycolysis is inhibited indirectly by inhibiting the transcription factor hypoxia-inducible factor 1α (HIF1α) which regulates the expression of key glycolytic genes including HK, pyruvate dehydrogenase kinase 1 (PDK1), phosphoglycerate kinase 1 (PGK1), GLUT1, glucokinase (GCK), and pyruvate kinase M1/2 (PKM2). The preferred HIF1α inhibitors include, but are not limited to, apigenin (aka LY-080400; NSC-83244; UCCF-031; or 4',5,7-trihydroxyflavone, 5,7-dihydroxy-2-(4-hydroxyphenyl)-4-benzopyrone), camptothecin (aka (+)-camptothecin; (+)-camptothecine; (S)-(+)-camptothecin; 20(S)-camptothecine; 21,22-secocamptothecin-21-oic acid lactone; camptothecine; or D-camptothecin), chrysin, curcumin (aka E 100; E-100; E100; INS NO. 100(l); INS-100 (l); NSC-32982; (E,E)-1,7-bis(4-Hydroxy-3-methoxyphenyl)-1,6-heptadiene-3,5-dione; diferuloylmethane; or diferulylmethane), epigallocatechin gallate, and GEN-27 (aka 5-hydroxy-7-(2-hydroxy-3-(piperidin-1-yl)propoxy)-3-(4-(2-hydroxy-3-(piperidin-1-yl)propoxy)phenyl)-4H-chromen-4-one).

In a further embodiment, the glycolysis inhibitor can be a selective or non-selective inhibitor of lactate dehydrogenase (LDH). General LDH inhibitors include, but are not limited to, galloflavin (aka 3,8,9,10-tetrahydroxy-pyrano[3,2-c][2]benzopyran-2,6-dione; or NSC 107022), and sodium oxamate (aka oxamic acid; aminooxoacetic acid sodium salt; oxalic acid monoamide sodium salt; or oxamic acid sodium salt). The preferred selective LDH-A inhibitors being, but not limited to, NHI-1 (aka 1-hydroxy-6-phenyl-4-(trifluoromethyl)-H-indole-2-carboxylic acid methyl ester; or methyl 1-hydroxy-6-phenyl-4-(trifluoromethyl)-1H-indole-2-carboxylate), FX-11 (aka 2,3-dihydroxy-6-methyl-7-(phenylmethyl)-4-propyl-1-naphthalenecarboxylic acid), galloflavin, and gossypol (aka 1,1',6,6',7,7'-hexahydroxy-5,5'-diisopropyl-3,3'-dimethyl-[2,2'-binaphthalene]-8,8'-dicarbaldehyde; 2,2'-bi[8-Formyl-1,6,7-trihydroxy-5-isopropyl-3-methylnaphthalene]; 2,2'-Bis(1,6,7-trihydroxy-3-methyl-5-isopropyl-8-aldehydonaphthalene); 7-(8-formyl-1,6,7-trihydroxy-3-methyl-5-propan-2-ylnaphthalen-2-yl)-2,3,8-trihydroxy-6-methyl-4-propan-2-ylnaphthalene-1-carbaldehyde).

In another embodiment, the glycolysis inhibitor is a PDK2 inhibitor. The preferred inhibitor being, but not limited to, DCA (aka dichloroacetate; dichloracetic acid; bichloracetic Acid; dichloroacetic acid sodium salt).

In an additional embodiment, the glycolysis inhibitor is a PKM2 inhibitor. The preferred inhibitors being, but not limited to, apigenin and shikonin (aka (±)-alkannin; (±)-shikalkin; (±)-shikonin; or (±)-5,8-dihydroxy-2-(1-hydroxy-4-methyl-3-pentenyl)-1,4-naphthoquinone).

In a specific embodiment, the glycolysis inhibitor blocks transketolase (TKT) and pyruvate dehydrogenase (PDH). The preferred inhibitor being, but not exclusively, oxythiamine (aka 5-(2-Hydroxyethyl)-3-(4-hydroxy-2-methyl-5-pyrimidinylmethyl)-4-methylthiazolium chloride).

The glycolysis inhibitor can be administered once daily or multiple times per day, daily, weekly or monthly. The glycolysis inhibitor can be administered simultaneously or sequentially from the DRD antagonist. The glycolysis inhibitor can be administered simultaneously or sequentially from the cholesterol lowering agent. The glycolysis inhibitor can be administered simultaneously or sequentially from the chemotherapeutic agent.

In an embodiment, the glycolysis inhibitor is 2-DG. In some additional embodiments, 2DG can be administered at a dose between about 5 to 500 mg/kg of body weight/week.

Cholesterol Lowering Agent

As indicated in the present disclosure, DRD antagonists increase cholesterol uptake/biogenesis in pancreatic cells and suppressing cholesterol uptake/biogenesis reduced pancreatic cell growth as well as tumor growth. As such, combining a DRD antagonist with a cholesterol lowering agent can be useful in the treatment of pancreatic cancer or pancreatitis.

Cholesterol lowering agents are therapeutic capable of reducing circulating cholesterol levels, especially circulating low-density lipoprotein (LDL) levels. In some embodiments, the cholesterol lowering agent is a HMG-CoA inhibitor capable of preventing the production of mevalonate from HMG-CoA either by directly inhibiting the enzyme or by downregulating its expression resulting in reduced biosynthesis of cholesterol and other isoprenoids.

Cholesterol lowering agents include, but are not limited to bile acid-binding resins, fibrates, vitamins, omega-3s, proprotein convertase subtilisin/kexin type 9 (PCSK9) inhibitors, cholesteryl ester transfer protein (CETP) inhibitors, inhibitors of intestinal cholesterol absorption, as well as HMG-CoA inhibitors.

In an embodiment, the cholesterol lowering agent can be an HMG-CoA inhibitor. HMG-CoA inhibitors (also known as statins) include, but are not limited to, lovastatin (aka MEVACOR®; ALTOCOR™; ALTOPREV®; (1S,3R,7S,8S,8aR)-1,2,3,7,8,8a-hexahydro-3,7-dimethyl-8-(2-(2R,4R)-(tetrahydro-4-hydroxy-6-oxo-2H-pyran-2-yl)ethyl)-1-naphthalenyl (S)-2-methyl-butyrate; 2β,6α-dimethyl-8alpha-(2-methyl-1-oxobutoxy)-mevinic acid lactone; 6α-methylcompactin; L-154803; MK-803; ML-530B; Act Lovastatin; Apo-lovastatin; Ava-lovastatin; or Dom-lovastatin), fluvastatin (aka LESCOL®; LESCOL XL®; Fluvastatin sodium; or Fluvastatin sodium ER), pravastatin (aka PRAVACHOL®; (+)-(3R,5R)-3,5-dihydroxy-7-[(1 S,2S,6S,8S,8aR)-6-hydroxy-2-methyl-8-{[(S)-2-methyl butyryl]oxy}-1,2,6,7,8,8a-hexahydro-1-naphthyl]heptanoic acid; Act Pravastatin; Bio Pravastatin; M-pravastatin; Ach-pravastatin; Ag-pravastatin; Apo-pravastatin; or Auro-pravastatin), rosuvastatin (aka Ezallor™; CRESTOR®; (3R,5S,6E)-7-(4-(4-fluorophenyl)-6-(1-methylethyl)-2-(ethyl (methylsulfonyl)amino)-5-pyrimidinyl)-3,5-dihydroxy-6-heptenoic acid; (3R,5S,6E)-7-{4-(4-fluorophenyl)-6-isopropyl-2-[methyl(methylsulfonyl)amino]pyrimidin-5-yl}-3,5-dihydroxyhept-6-enoic acid; rosuvastatin calcium; rosuvastatin zinc; Act rosuvastatin; Crestor; Ach-rosuvastatin; Ag-rosuvastatin; or Apo-rosuvastatin), atorvastatin (aka LIPITOR®; atorvastatin calcium; atorvastatin calcium trihydrate; Ach-atorvastatin Calcium; Ag-atorvastatin; or Apo-atorvastatin), pitavastatin (aka LIVALO®; NIKITA®; Zypitamag™; Pitavastatin calcium; or Pitavastatin magnesium), simvastatin (aka ZOCOR®; FLOLIPID®; 2,2-dimethylbutyric acid, 8-ester with (4R,6R)-6-(2-((1S,2S,6R,8S,8aR)-1,2,6,7,8,8a-hexahydro-8-hydroxy-2,6-dimethyl-1-naphthyl)ethyl)tetrahydro-4-hydroxy-2H-pyran-2-one; Act Simvastatin; Bci Simvastatin; Ag-simvastatin; Apo-simvastati; MK 733; MK-0733; or MK-733), cerivastatin (aka BAYCOL®; Cerivastatin sodium; Lipobay; or Rivastatin), and mevastatin (aka COMPACTIN®; ML 236B; CS 500; ML 236 B; or ML-236B).

The cholesterol lowering agent can be administered once daily or multiple times per day, daily, weekly or monthly. The cholesterol lowering agent can be administered simultaneously or sequentially from the DRD antagonist. The cholesterol lowering agent can be administered simultaneously or sequentially from the glycolysis inhibitor. The cholesterol lowering agent can be administered simultaneously or sequentially from the chemotherapeutic agent.

In an embodiment, the cholesterol lowering agent is atorvastatin. In some additional embodiments, atorvastatin can be administered at a dose between about 1 to 250 mg, or between about 5 to 100 mg.

Chemotherapeutic Agent

In one further embodiment the aforementioned described antagonist for use in the treatment of pancreatic cancer or chronic pancreatitis can be administered in combination with at least one additional anti-cancer drug, such as a chemotherapeutic agent, which preferably is known to be effective against pancreatic cancer, such as gemcitabine.

In context of the present disclosure it was surprisingly found that using a dopamine receptor antagonist such as pimozide, a glycolysis inhibitor such as 2-DG and a cholesterol lowering agent such as atorvastatin can enhance the anti-proliferative activity of other pancreatic cancer drugs such as gemcitabine. In some embodiments, gemcitabine is administered by the intravenous route. Dose ranges from 0.5 to 2, preferably 1-1.2 g/m$^2$ of body surface area. Drug doses can be adjusted according to the methods known in the art.

In a specific embodiment, the chemotherapeutic agent or anti-cancer drug is a mitotic inhibitor, e.g. ABRAXANE® (also known as Paclitaxel Albumin-stabilized Nanoparticle Formulation; or [(1 S,2S,3R,4S,7R,9S,10S, 12R, 15S)-4,12-diacetyloxy-15-[(2R,3S)-3-benzamido-2-hydroxy-3-phenylpropanoyl]oxy-1,9-dihydroxy-10,14,17,17-tetramethyl-11-oxo-6-oxatetracyclo[11.3.1.03,10.04,7]heptadec-13-en-2-yl] benzoate)).

In an another embodiment, the chemotherapeutic agent or the anti-cancer drug is a DNA synthesis inhibitor. The anti-cancer drug is selected from the group consisting of XELODA® (also known as capecitabine; pentyl N-[1-[(2R,3R,4S,5R)-3,4-dihydroxy-5-methyloxolan-2-yl]-5-fluoro-2-oxopyrimidin-4-yl]carbamate; 5'-deoxy-5-fluorouridine; 5'-DFUR; 5-Fluorouracil)), Gemcitabine (also known as Infugem; or 4-amino-1-[(2R,4R,5R)-3,3-difluoro-4-hydroxy-5-(hydroxymethyl)oxolan-2-yl]pyrimidin-2-one), MUTAMYCIN® (also known as Mitomycin C, MITOSOL®; [(4S,6S,7R,8S)-11-amino-7-methoxy-12-methyl-10,13-dioxo-2,5-diazatetracyclo[7.4.0.02,7.04,6]trideca-1(9),11-dien-8-yl]methyl carbamate, and Eloxatin (also known as Oxaliplatin (also known as Eloxatin; [(1R,2R)-2-azanidylcyclohexyl]azanide;oxalate;platinum(4+)).

XELODA® can be combined with folinic acid (also known as Leucovorin; Levoleucovorin; 5-formyl tetrahydrofolic acid; (2S)-2-[[4-[(2-amino-5-formyl-4-oxo-3,6,7,8-tetrahydropteridin-6 yl)methylamino]benzoyl]amino] pentanedioic acid to reduce side effects.

In an additional embodiment, the anticancer agent or the chemotherapeutic is a kinase inhibitor, e.g. AFINITOR® (also known as AFINITOR DISPERZ®; or EVEROLIMUS®).

In a specific embodiment, the chemotherapeutic agent or anti-cancer drug is a topoisomerase I inhibitor, e.g. Onivyde™ (also known as CAMPTOSAR®; or [(19S)-10,19-diethyl-19-hydroxy-14,18-dioxo-17-oxa-3,13-diazapentacyclo[11.8.0.02,11.04,9.015,20]henicosa-1(21),2,4(9),5,7,10,15(20)-heptaen-7-yl] 4-piperidin-1-ylpiperidine-1-carboxylate).

In yet another embodiment, the anti-cancer drug is a receptor tyrosine kinase (RTK) inhibitor such as, but not limited to, SUTENT® (also known as Sunitinib malate or N-[2-(diethylamino)ethyl]-5-[(Z)-(5-fluoro-2-oxo-1H-indol-3-ylidene)methyl]-2,4-dimethyl-1H-pyrrole-3-carboxamide). In a specific embodiment, the RTK is epidermal growth factor receptor (EGFR) and the inhibitor can be Tarceva (also known as Erlotinib hydrochloride or N-(3-ethynylphenyl)-6,7-bis(2-methoxyethoxy)quinazolin-4-amine).

In a specific embodiment, the combination therapy for PDAC is pimozide or haloperidol, 2-DG, atorvastatin, and gemcitabine.

The combination of the present disclosure provides advantages to state of the art cancer or chronic pancreatitis treatments. The examples show that the combination of a dopamine receptor antagonist enhances the activity of another pancreatic cancer drug. Therefore, the combination will have the advantage that the individual combination compounds can be used in lesser amounts which reduces the occurrence of adverse effects. Also the combinations of the disclosure provide synergistic activity as the sum of their individual effects is lower than the effect of the combination. Therefore, the combination of the disclosure in a preferred embodiment of this aspect comprises the combination compounds in synergistically effective amounts.

The combinations described herein can be used in combination with other therapies (cellular therapy, radiation therapy, etc.) known or suspected to benefit subjects afflicted with pancreatitis or pancreatic cancer.

Pharmaceutical Formulations

Yet another aspect of the disclosure pertains to a pharmaceutical formulation (or composition which means the same in this context), comprising an antagonist of a dopamine receptor as described above, or a combination as described above, optionally together with pharmaceutically acceptable excipients and/or carriers.

The terms "pharmaceutical formulation", "pharmaceutical composition" and "medicament" are used interchangeably herein, and comprise the antagonists or combinations of the present disclosure and optionally one or more pharmaceutically acceptable carrier and/or excipient. The compounds of the present disclosure can be formulated as pharmaceutically acceptable salts. Acceptable salts comprise acetate, methylester, HCl, sulfate, chloride and the like. The medicaments are, preferably, administered topically or systemically. Suitable routes of administration conventionally used for drug administration are intratumoral, peritumoral, oral, intravenous, or parenteral administration as well as inhalation. However, depending on the nature and mode of action of the compound, the medicaments may be administered by other routes as well. For example, polynucleotide compounds may be administered in a gene therapy approach by using viral vectors, viruses or liposomes.

The present disclosure provides in a further aspect also a method for treating or preventing pancreatic cancer or chronic pancreatitis in a subject in need of such a treatment, the method comprising the administration of an antagonist of a dopamine receptor as described above, or a combination as described above.

The term "prevention" or "preventing" refers to retainment of health with respect to the disease (pancreatic cancer or chronic pancreatitis) or the symptoms referred to herein for a certain period of time in a subject. It will be understood that the said period of time is dependent on the amount of the drug compound which has been administered and individual factors of the subject. It is to be understood that prevention may not be effective in all subjects treated with the compound according to the present disclosure. However, the term requires that a statistically significant portion of subjects of a cohort or population are effectively prevented from suffering from a disease or the symptoms referred to herein. Preferably, a cohort or population of subjects is envisaged in this context which normally, i.e. without preventive measures according to the present disclosure, would develop a disease or symptoms as referred to herein. Whether a portion is statistically significant can be determined without further ado by the person skilled in the art using various well known statistic evaluation tools discussed above. Preferably, prevention shall be effective for at least 60%, at least 70%, at least 80%, or at least 90% of the subjects of a given cohort or population.

Diagnostic and Imaging Methods

The present disclosure provides a method comprises the steps of:
a. Providing a biological sample derived from the pancreas of said subject,
b. Detecting the presence or absence of a dopamine receptor (preferably DRD2) in said biological sample, wherein the presence of said dopamine receptor (preferably DRD2) in said biological sample is indicative for the presence of pancreatic tumor cells and/or chronic pancreatitis. These steps can be performed prior to the administration of the DRD antagonist, the glycolysis inhibitor and the cholesterol lowering agent to determine if the combination could be useful in the subject intended to be treated.

The expression of dopamine receptors, namely DRD2, in pancreatic cancer tissue and chronic pancreatitis is for the first time described herein. Therefore, dopamine receptors, and DRD2 in particular, provide a novel biomarker for the diagnosis of the presence of cancer cells of pancreatic origin. In addition, the identification of dopamine receptor expression in a sample from a subject does not only allow for the diagnosis of pancreatic cancer, it also provides the clinical practitioner with the information that this cancer may be treated with antagonists of dopamine receptors. Diagnosing in context of the herein describe disclosure therefore also relates to the assessment of treatment options for a pancreatic cancer patient.

In a preferred embodiment of the method of the disclosure said biological sample is a pancreatic tissue sample, preferably a pancreatic ductal tissue sample. For example this sample may be an immersion fixed paraffin embedded tissue sample.

The method of the disclosure in preferred embodiments furthermore includes in step b. that DRD2 is detected directly, for example immunohistochemically, or indirectly by detecting DRD2 mRNA expression.

The diagnostic methods of the disclosure is preferably an ex vivo or in vitro method.

"Subjects" in this context are preferably a mammal, preferably a human. The subject is maybe suspected to carry pancreatic cancer or suffer from chronic pancreatitis. In this context the method of the disclosure seeks to establish a first diagnosis of the presence of pancreatic cancer or chronic pancreatitis. Also the method includes scenarios where the tissue of a resected pancreatic tumor is assayed for the presence or expression of a dopamine receptor antagonist. In this regard, although the diagnosis of pancreatic cancer or chronic pancreatitis is already established, the presence or expression of a dopamine receptor is indicative for a successful treatment with an antagonist of a dopamine receptor. The above general descriptions regarding the first and second aspects of the disclosure of course also apply for the diagnostic aspects.

Finally provided is in another aspect a diagnostic kit for detecting pancreatic tumor cells or chronic pancreatitis, comprising means for performing a method as described herein above, preferably means for the detection of DRD2, such as nucleic acid probes or antibodies, together with appropriate buffers and solutions. Such means are well known to the person of skill.

The present disclosure provides a method comprises the steps of:
 a. Administering at least one labelled imaging reagent to the subject,
 b. Detecting the presence and/or location of the imaging reagent in the subject.

These steps can be performed prior to the administration of the DRD antagonist, the glycolysis inhibitor and the cholesterol lowering agent to determine if the combination could be useful in the subject intended to be treated. The method can include specifically imaging the pancreas of the subject after the at least one imaging reagent has been administered to the subject.

In the context of the present disclosure, the imaging reagents that can be used for the imaging pancreatic cancers and pancreatitis. The imaging reagents are the DRD2 antagonist, the glycolysis inhibitor and/or the cholesterol lowering agent are coupled (i.e., physically linked) to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin, green, yellow or red fluorescent protein; an example of a luminescent material includes luminol; examples of bioluminescent materials include luciferase, luciferin, and aequorin, and examples of suitable radioactive materials include $^{125}I$, $^{131}I$, $^{35}S$, $^{32}P$ or $^3H$.

The present invention will be more readily understood by referring to the following examples which are given to illustrate the invention rather than to limit its scope.

EXAMPLES

Materials and Methods

Study Population and IHC

Tissue microarray (TMA) slides of human pancreatic tissue samples were included with 63 cases of Pancreatic Ductal Adenocarcinoma (PDAC), 49 cases of chronic pancreatitis (CP) and 40 of healthy pancreatic tissues (Normal) from non-cancer patients.

Immunohistochemistry (IHC) on TMA slides pursued with boiling the samples two times in citrate buffer (10 mM) for 10 min and suppressing of peroxidase with the solution of $H_2O_2$ (3%) in 30% methanol. Slides were incubated overnight with a dilution of anti-DRD2 antibody (1:50) and IgG2b (1:375) as a negative control at 4° C. TBS-T buffer solution was used to wash antibodies out from the unbounded target proteins and then, slides exposed to the anti-mouse HRPO conjugated secondary antibody at room temperature for 1 h. Diaminobenzidine peroxidase substrate was used to yield intense dark brown color for detection of target protein and Mayer's hematoxylin solution to stain the nuclei. Sections were scanned with ScanScope GL System (Aperio Technologies, Vista, USA) and two pathologists independently checked the results to detect ductal structures and quality of staining in the samples.

Cell Lines and Treatment Reagents

Five pancreatic ductal cancer cell lines with various degree of differentiation were obtained from American Type Culture Collection (Rockville, USA) and Normal Human Dermal Fibroblasts (NHDF) obtained from PromoCell. BXPC-3 (moderately differentiated) as well as poorly differentiated human pancreatic cancer cell lines, PANC-1 and MIAPaCa-2, have been established from primary tumor. AsPC-1, CAPAN-1 and CFPAC-1 which represent well differentiated cell lines was isolated from ascites and liver metastasis of pancreas adenocarcinoma. All cell lines contain mutation in P53 whereas K-ras mutation reported in all with the exception of BxPc3. BRCA2 mutation just reported in CAPAN-1 cells.

MiaPaCa2 and PANC-1 were maintained in DMEM medium, NHDF and CFPAC1 in IMDM medium and BxPc3, AsPC-1 and CAPAN1 in RPMI 1640 medium supplemented with 10% (v/v) heat-inactivated fetal bovine serum, 100 µg/ml streptomycin and 100 U/ml penicillin. They were maintained in humid environment with 5% $CO_2$ at 37° C.

Pimozide and Haloperidol (DRD2 antagonists), L-741, 626 (selective DRD2 antagonist) and Atorvastatin were purchased from Sigma Aldrich. They suspended in DMSO to make a stock solution and stored at −20° C. A stock solution of 2-Deoxy-D-glucose and Gemcitabine (Sigma Aldrich) in water stored at −20° as well. For non-specific solvent effect on cells, same concentration of DMSO was used as a control and its concentration did not overpass 0.2% in all treatments.

TABLE 1

Used cell lines and their origin

| Cell Lines | K-ras | BRCA2 Mut | P53 Mut | Cell Source | Cell type | Differentiation |
|---|---|---|---|---|---|---|
| BXPC-3 | − | − | + | Primary tumor | Ductal | Moderate |
| CAPAN1 | + | + | + | Liver metastasis | Ductal | Well |
| CFPA-1 | + | − | + | Liver metastasis | Ductal | Well |
| MIAPaCa-2 | + | − | + | Primary tumor | Ductal | Poor |
| PANC-1 | + | − | + | Primary tumor | Ductal | Poor |
| Fibroblast | − | − | − | Primary cell | Normal | − |
| AsPC-1 | + | − | + | Ascites | Ductal | Well |

Sulforhodamine B Cytotoxicity and Colony Formation Assay

Sulforhodamine B sodium salt (sigma) was used to assess cell viability and $IC_{50}$ determination of pancreatic cancer cells. Briefly, cells were placed in 96 well plates and allowed to settle for 24 h. Cell medium was aspirated and fresh medium with or without different increasing dosage of antagonists or gemcitabine were added on them. After 24, 48 and 72 h of treatment, cell medium of each wells replaced with 200 μL of cell fixative reagent 10% (w/v) trichloroacetic acid (TCA). After incubation of plate in 4° C. for 3 h, the fixed cells washed with water and allow them to dry in 37° C. for 1 h. 50 μL of 0.4% (w/v) SRB staining solution (Sulforhodamine B solved in 0.1% acetic acid) was added in each well to completely cover the cells. Experiment was followed by washing the cells from unbounded SRB after 30 min of incubation in room temperature with 0.1% acetic acid. Cells were then dried and SRB which was bound with mammalian cell protein dissolved with 100 μL of 10 mM Tris-base solution (TBS). Cell viability was specified by using plate reader (TECAN) with measuring of absorbance at 570 and 650 nm (background) in treated or untreated 96 well plate.

For colony formation assay, cells infected with lentiviral supernatants were trypsinized and plated in a 6 well plate as single cells (1 000 cells per well). Cells were allowed to attach 24 h and then they were treated with puromycin. Media was removed every 4 days, the cells washed once and fresh media added. Colony formation assays continued for an additional 10 (for pLKO) or 28 days (for DRD2$^{KD}$). Upon colony formation, the medium was aspirated and the cells washed with PBS. Afterward, the cells were fixed for 10 min by adding 100% methanol. The methanol was then removed and replaced with 0.1% (v/v) crystal violet staining solution for 1 h in order to visibly colonies.

Plasmids and Viral Transduction

All lentiviral shRNA vectors were retrieved from the arrayed MISSION® TRC genome-wide shRNA collections purchased from Sigma-Aldrich Corporation. Additional information about the shRNA vectors can be found at http://www.sigmaaldrich.com/life-science/functional-genomics-and-rnai/shrna/library-information.html or http://www.broad.mit.edu/genome_bio/trc/rnai.html, using the TRCN number. The following lentiviral shRNA vectors targeting DRD2 were used: TRCN0000011342 (shDRD2 #5) and TRCN0000011343 (shDRD2 #4). HEK293T cells were used as producers of lentiviral supernatants and the calcium phosphate method was used for the transfection of this cells which described at http://www.broadinstitute.org/rnai/public/resources/protocols. Infected cells by lentiviral supernatants were selected for successful lentiviral integration using 2 mg/ml of puromycin.

Wound Healing Assay for Cell Migration

PANC-1 cells were seeded into the 35 mm-dish culture-silicon Insert frames from Ibidi where already attached to the 6 well culture plate. When 96-98% confluency was achieved, the insert frames were removed using sterile forceps to reach cell free gap. To create a reference point for subsequent measurements, three different part of the gap was marked on the underside of the plastic. Floating cells and cell debris were washed using PBS, relative culture medium was added to each wells and migration distance was photographed using a Zeiss Axiovert 24 light microscope at zero time in the marked areas. Afterward, the wells were treated by addition of DMSO as control and different increasing concentration of Pim and L741. Plates were then placed into the incubator and the cells were allowed to migrate until the time when the gap for the positive control closed (t time). Images were taken from the marked areas again. This assay was performed employing various concentrations of drugs at which maximum 5% viability inhibition was observed after 10 h treatment.

Transwell Migration Assay

This assay for confirmation of cell migration was performed using 96-well Costar Transwell chambers with 8.0 μm pore polycarbonate membranes (Corning Inc., Corning, N.Y.). Cell culture inserts transwells were placed in wells of 96 well plate. The bottom chambers were filled with 120 μl of cell culture medium containing 10% FBS. Cells suspended in 70 μl serum free medium with DMSO as negative control or drugs were added to the upper part of each chamber followed by incubation at 37° C. with 5% $CO_2$. After 4 h the medium was aspirated from the top of chambers and the bottom side of chambers washed with PBS. Those that have penetrated to the bottom side of the membrane were detached with 0.25% tryspin/EDTA during 3 min (37° C.) followed by inactivation of trypsine with soybean (Sigma Aldrich). To compare the number of invaded cells in treatment conditions to the control untreated cells the CELLTITER-GLO® Luminescent cell viability assay were conducted. Six replicates were performed for each treatment condition to predict the responder outcome variable and the luminescence signal which is corresponding to the number of live suspended cells was measured. Graph was plotted according to the readings obtained. This assay was performed employing various concentrations of drugs at which maximum 5% viability inhibition was observed after 4 h treatment.

Quantitative Real-Time Polymerase Chain Reaction

For mice xenograft tissue samples and cultured cells, the miRNeasy kit (Qiagen, Valencia, Calif.) was used to extract total RNA. Reverse transcription was done using the Maxima First Strand cDNA Synthesis Kit for RT-qPCR (Thermo Scientific Rockford, Logan, Utah). Real-time polymerase chain reaction was run using the ViiA 7 Real-Time PCR System (Applied Biosystems, Darmstadt, Germany) and the FastStart Universal SYBR Green Master Mix (Roche Diagnostics, Mannheim, Germany) according to the manufacturers' specifications. Relative messenger RNA levels were normalized to the expression of the housekeeping gene. Quantification values were calculated according to a standard curve method created from a dilution series. Polymerase chain reactions were performed in triplicate.

Tumor Growth of DRD2 Knockdown Pancreatic Cancer Cells in NGS Mice

Severe combined immunodeficient beige mice were bred in-house. One million Panc-1 cells transduced with shDRD2

5, shDRD2 #4, or pLKO were suspended in 150 µL phosphate-buffered saline and mixed with 150 µL Matrigel (BD Biosciences, San Jose, Calif.) before the respective suspension was injected subcutaneously into the left and right flank of a mouse. For each test cell line, 3 mice were injected with cells in both flanks. Tumor size was determined twice a week using a caliper to measure the volume of the tumor according to the formula: volume (V)=length (L)×depth (D)×width (W). After reaching the appropriate volume, primary tumors were resected. In case of pLKO, this happened on day 51 after injection; for shDRD2 #1 and shDRD2 #2 the tumor was removed after 65 days. Tumors were embedded in paraffin after zinc fixation for immunohistochemistry and H&E staining, or stored at −80° C. for RNA extraction Tumor Growth of Orthotopic Pancreatic Tumor Mouse Model Treated with DRD2 Antagonism Two million MIAPaCa-2 cells were resuspended in 10 µL Matrigel (BD Biosciences, San Jose, Calif.) were orthotopically implanted into the tail of the pancreas of 6-week-old Nod scid gamma animals (Jackson Labs, Bar Harbor, Me.) (day 1). When tumors were palpable (day 27), mice were randomized into 2 groups (n=7 in control group and n=9 in haloperidol group) and injected intraperitoneally with either haloperidol (10 mg/kg) or solvent (dimethylsulfoxide [DMSO] control group) for 12 days. The experiment was terminated when control mice appeared moribund. Weight of the animal and final tumor weight and volume were measured.

Combination Therapy in NSG Mice

NOD severe combined immunodeficiency gamma (NSG) mice were subcutaneously injected in the right flank with five million MIAPaCa-2 cells. Once tumors were detectable (200 mm$^3$), mice were randomized into 8 groups (5 in each group) and treated through intraperitoneal injection as indicated for 16 days. All drugs were given every day whereas gemcitabine was given every 4 days, alone or in combination. Experiment was terminated when control animals became moribund. The growth of tumors was measured every 4 days. Tumors were harvested and photographed. Tumor weights and volumes were measured.

Free Cholesterol Measurement in Cancer Cells

Cancer cells were seeded for 24 hours and treated with pimozide, haloperidol or DMSO for 18 hours. The cells were fixed with paraformaldehyde, stained with Filipin™ and propidium iodide (PI), and photographed. Filipin™ is a fluorescent polyene antibiotic that binds to free cholesterol. Also, PI used to visualize the nucleus. The images generated were subjected to densitometric analysis using the ImageJ software.

Glucose Uptake Measurement

The induction effect of pimozide or haloperidol on labeled 2-DG uptake in cancer cells were determined from measurement of the fluorescence intensity of cell lysates. Briefly, 10 million suspended cancer cells were washed with PBS, pre-incubated with either pimozide or haloperidol for 30 min and then incubated with 50 mM labeled 2-DG for another 1 hour at 37° C. The cells were centrifuged and washed 2 times with cold PBS. Cell pellets were then lysed and the fluorescence intensity of cell lysate was measured on a Tecan Infinite F200™ Microplate Reader.

Figure 1A:
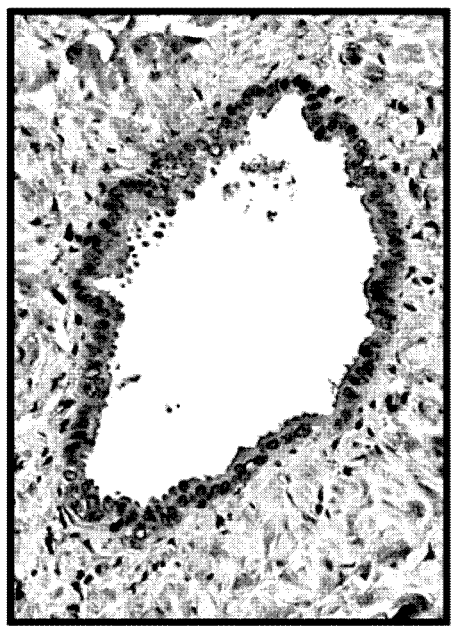
FIGS. 1A to 1C provide an immunohistochemical (IHC) analysis of DRD2 levels in clinical tissues. Representative examples of DRD2 expression in duct part of normal pancreas (FIG. 1A), chronic pancreatitis (CP) (FIG. 1B) and pancreatic ductal adenocarcinoma (PDAC) (FIG. 1C) in clinical tissues using antibody against DRD2 are shown. Normal ductal cells are almost DRD2 negative, CP lesion and PDAC represented with moderate and strong DRD2 expression, respectively.
Figure 1B:
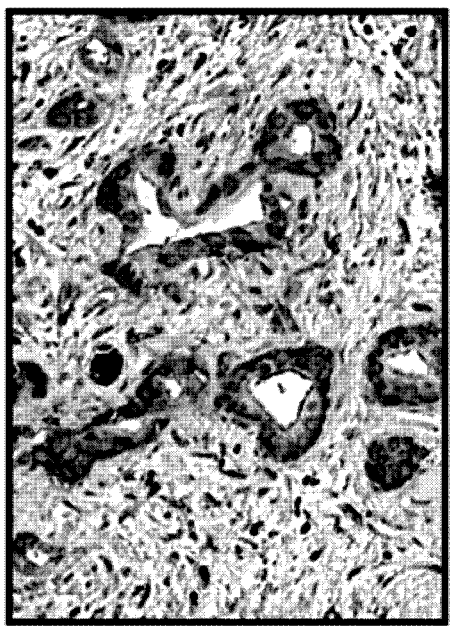
Figure 1C:
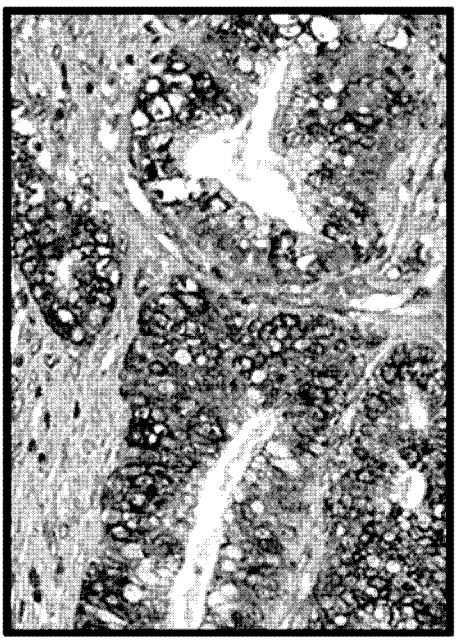

Example 1: Specific Detection of DRD2 in Chronic Pancreatitis and Pancreatic Cancer and not in Healthy Tissue FIG. 1 shows that DRD2 was detected in immersion fixed paraffin-embedded sections of pancreatic ductal cancer tissue 1(C) and chronic pancreatitis (B) but not in normal ductal cells 1(A) using a human monoclonal antibody. Tissues were then counterstained with hematoxylin.

Example 2: Immunohistochemical Analysis of DRD2 Levels Using a Large Number of Clinical Tissues, Tissue Microarray (TMA)

Figure 2:
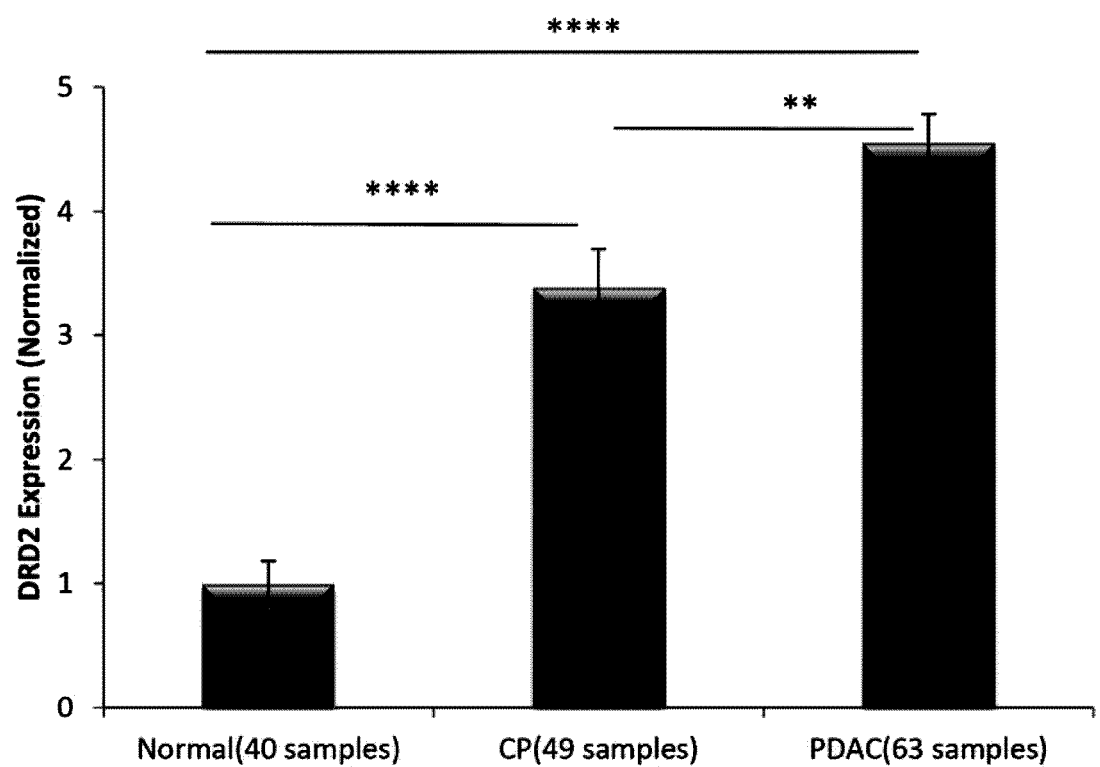
FIG. 2 shows quantification of the immunohistochemical analysis of DRD2 levels using a large number of clinical tissues, Tissue Microarray (TMA). Distribution of DRD2 expression in clinical tissues revealed its high expression in PDAC and CP in comparison with mild positivity in pancreatic ducts normal samples.

Distribution of DRD2 expression in clinical tissues revealed its high expression in PDAC and CP in comparison with mild positivity in pancreatic ducts normal samples (FIG. 2).

Example 3: Antagonists of DRD2 were Cytotoxic to Pancreatic Cancer Cells

Figure 3A:
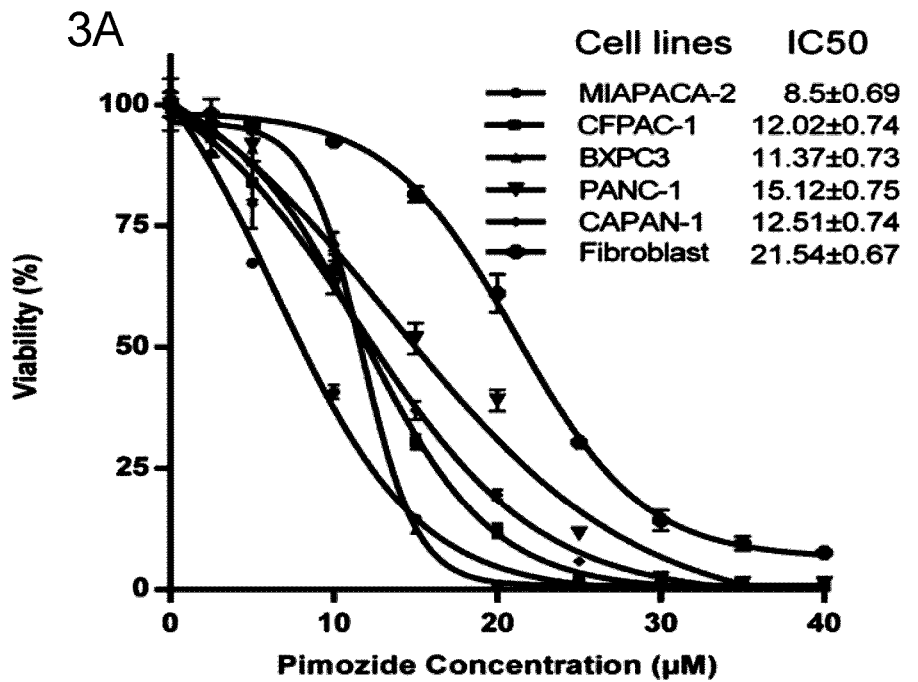
FIGS. 3A and 3B show the dose dependent toxicity effect of Pimozide and L741,626 (L741) on PDAC cell. PANC-1, CFPAC-1, CAPAN-1, MIAPaCa-2, BXPC-3 and fibroblast cells were seeded for 24 h and were exposed to increasing concentration of Pimozide and vehicle for 72 h (FIG. 3A). The same procedure was followed for treatment of cancer cell lines with L741 (FIG. 3B). Cell viability was characterized using a SRB assay. Values are the mean+/−SD of six independent experiments.

Potent toxicity effect of Pimozide, an FDA-approved drug and DRD2 antagonist, on the viability of pancreatic cancer cell lines (see FIG. 3A). The effect was specific to cancer cells but not as much to Fibroblast (non-cancer cells).

Figure 3B:
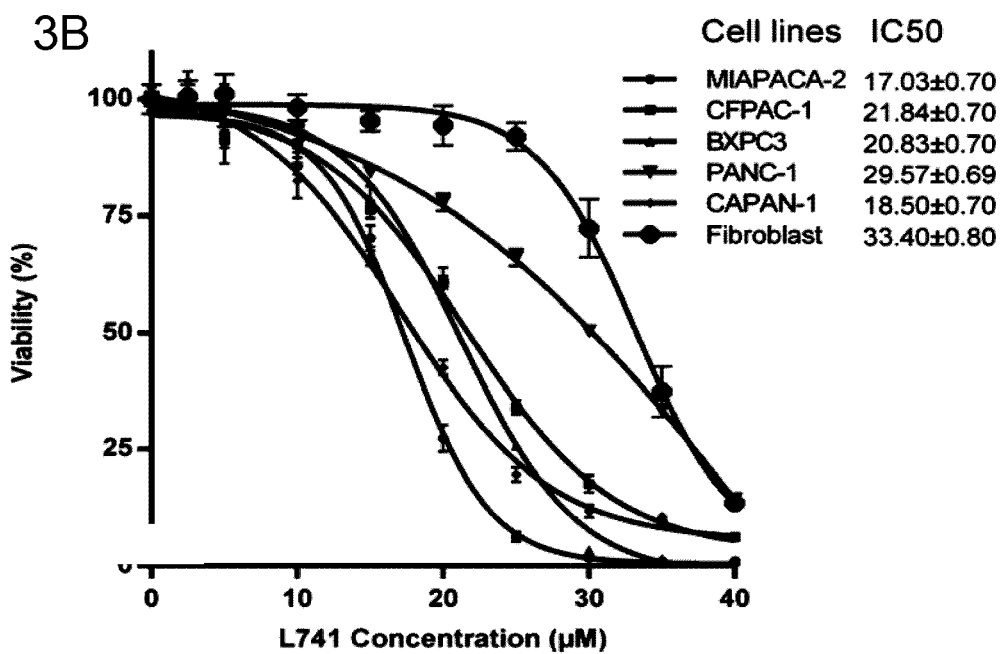

The effect of pimozide was reproduced with another more selective DRD2 antagonist. Specific toxicity effect of L741, 626, a selective DRD2 antagonist, on the viability of pancreatic cancer cell lines is shown in FIG. 3B, and supported the finding that antagonists of dopamine receptors, in particular DRD2, were beneficial for a cancer treatment.

Figures 4A, 4B:
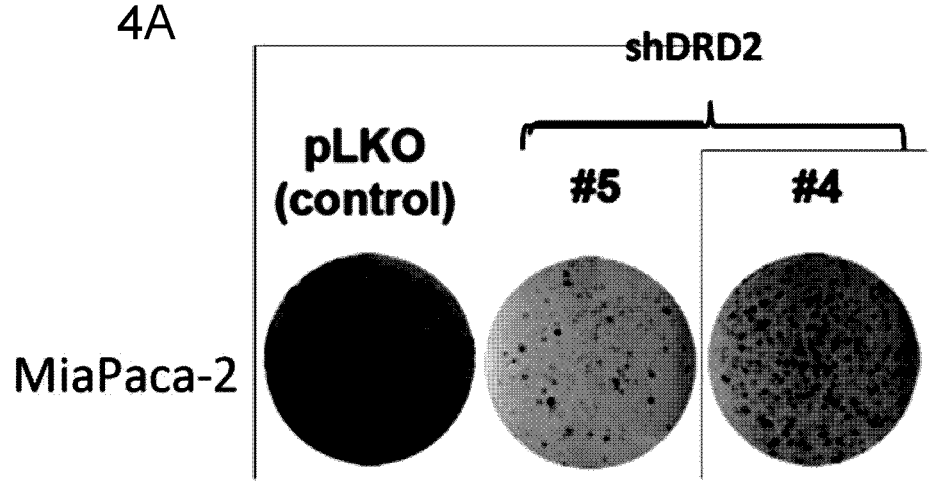
FIGS. 4A and 4B show that independent shRNAs targeting DRD2 sensitizes pancreatic cancer cells to their antitumor effects. Colony formation assay of MIAPaCa-2 (FIG. 4A) and PANC-1 (FIG. 4B) cells that express pLKO as a control or independent lentiviral shDRD2 vectors (#4 and #5) were performed. The cells were fixed, stained, and photographed after 10 (pLKO) or 28 days (shDRD2).

In order to assess whether the effect observed with pimozide and L-741,626 was indeed due to the action of DRD2, an RNAi experiment was conducted. Using shRNA targeting DRD2 expression is shown in FIGS. 4A and 4B. Also the RNAi construct significantly impaired tumor cell growth and viability compared to a control treatment.

All lentiviral shRNA vectors were retrieved from the arrayed MISSION® TRC genome-wide shRNA collections purchased from Sigma-Aldrich Corporation. Additional information about the shRNA vectors can be found at http://www.sigmaaldrich.com/life-science/functional-genomics-and-rnai/shrna/library-information.html or http://www.broad.mit.edu/genome_bio/trc/rnai.html, using the TRCN number. The following lentiviral shRNA vectors targeting DRD2 were used: TRCN0000011342 and TRCN0000011343. Lentiviral supernatants were generated as described at http://www.broadinstitute.org/rnai/public/resources/protocols.

Example 4: Combination Treatment of DRD2 Antagonists Pimozide with Gemcitabine

Figure 5:
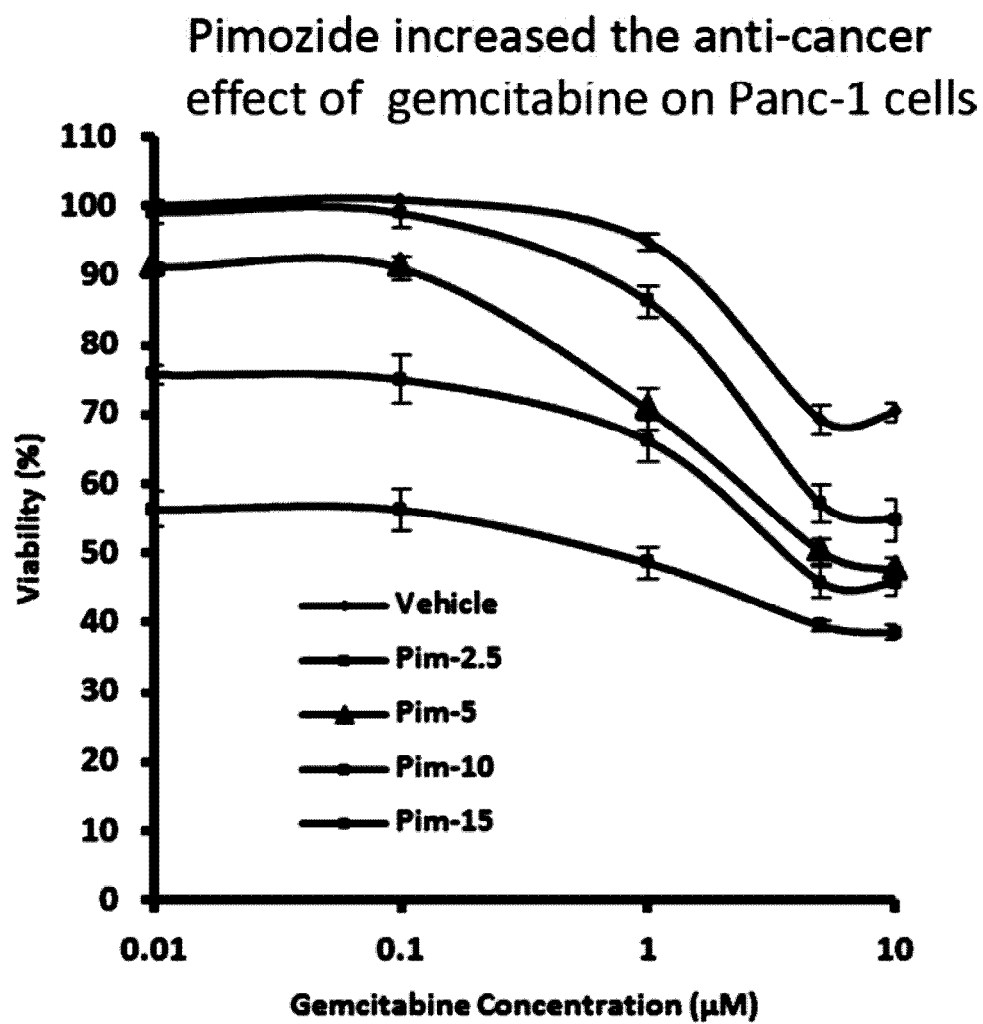
FIG. 5 shows the effect of increasing concentrations of gemcitabine and/or pimozide on PANC-1 cell growth. PANC-1 was seeded for 24 h and was exposed to different concentration of Gemcitabine, Pimozide or combination of them for 72 h. Cell viability was characterized using a SRB assay. Values are the mean+/−SD of six independent experiments.

Interestingly the use of increasing concentrations of pimozide in combination with a variety amount of gemcitabine in PANC-1 cells (FIG. 5).

Example 5: Inhibition of DRD2 Reduced Migration Capacity of Tumor Cells

Figures 6A, 6B:
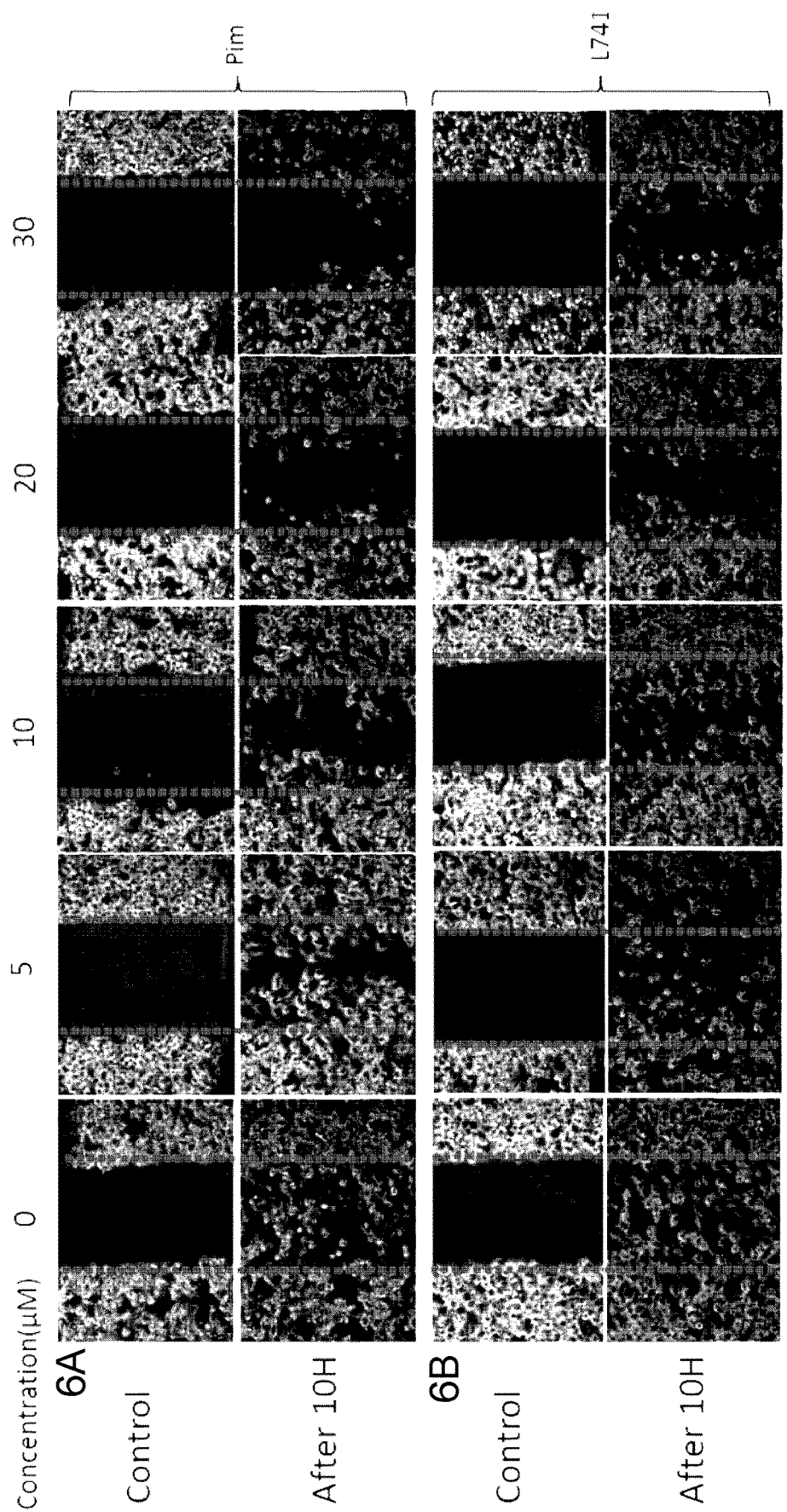
FIGS. 6A and 6B show a dose dependent inhibitory effect of Pimozide and L741 on migration of PDAC cells in a wound healing assay. PANC-1 cells were platted in the chamber were already attached in 12 well plate and allowed to grow for 24 h. Then, a wound was made in the confluent monolayer by removing the chamber. Cells were exposed to increasing concentration of Pimozide (FIG. 6A) or L741 (FIG. 6B) and vehicle for 10 h. Wound gap closure was measured for each drug concentration by comparing the gap at time 0 h to the one at the time 10 h when the gap closed in negative control and normalized to untreated condition.

PANC-1 tumor cell migration was tested in a scratching assay using pimozide and L-741,626 in increasing concentrations. Results are depicted in FIG. 6. The results indicated that tumor cell migration was affected by both pimozide and L-741,626 in a concentration dependent manner.

The impact on migration capacity of DRD2 antagonists was reproduced using PANC-1 and a different cell line (MIAPaCa-2) in a Boyden Chamber Assay. Results are depicted in FIG. 7. Pimozide significantly reduced migrated cells both in the PANC-1 and MiaPac-2 cell line, in a concentration dependent manner.

Hence, the inhibition of DRD2 in pancreatic tumor cells not only reduced tumor cell viability and survival, but also reduced migrating cells which is beneficial to avoid the development of pancreatic metastasis.

Example 6: In Vivo Inhibition of Tumor Growth

In order to monitor tumor growth in an in vivo situation mice were implanted with PANC-1 cells expressing the negative control (pLKO) or shDRD2 (three mice per group, each implanted with cells in both flanks). There was a significant decrease in tumor growth in mice implanted with DRD2-deficient cells (p=0.002) as can be seen in FIG. 8A. Staining for Ki-67, a marker of cell proliferation, confirmed decreased proliferation in DRD2-deficient cells. Analysis with an antibody against DRD2 confirmed the efficacy of knockdown (FIG. 8B).

Therefore, DRD2 inhibition significantly reduced pancreatic tumor growth in vivo.

Example 7: Additional Combination Therapy

Figure 9A:
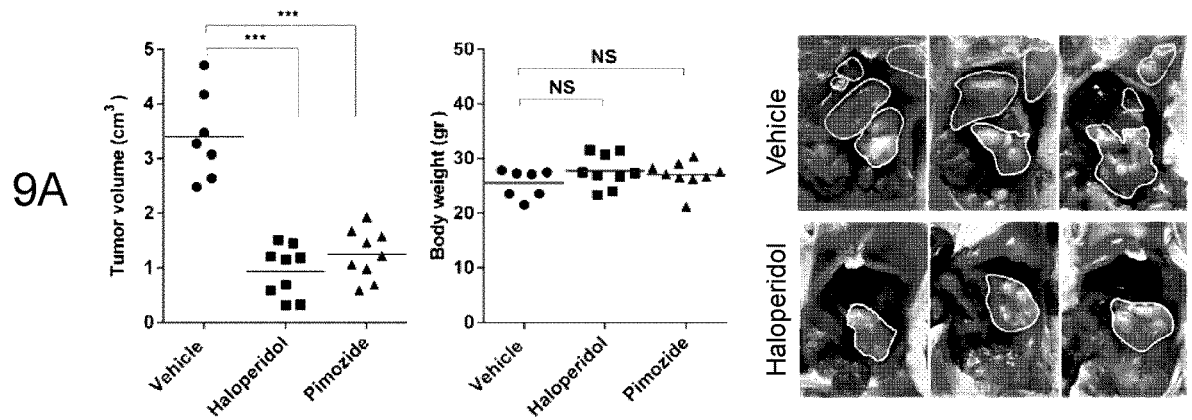
FIGS. 9A and 9B show that DRD2 antagonism by pharmacological means reduces tumor volume, metastasis, and viability. Effects of DRD2 antagonists haloperidol (black square) and pimozide (black triangle) on tumor volume (left) and animal body weight (middle) depicted on the y-axis compared to vehicle (black dots) and metastatic dissemination (highlighted by yellow outlines in right) (FIG. 9A). Dose-dependent effects (x-axis) of DRD2 antagonists pimozide (left), haloperidol (middle) and L-741 (right) on viability displayed on the y-axis of primary (KPC-023, green line gray diamond; KPC-01, brown line gray asterisk) and metastatic (KPC-LM, red line gray triangle) pancreatic cancer cell lines isolated from KPC mice (FIG. 9B).
Figure 9B:
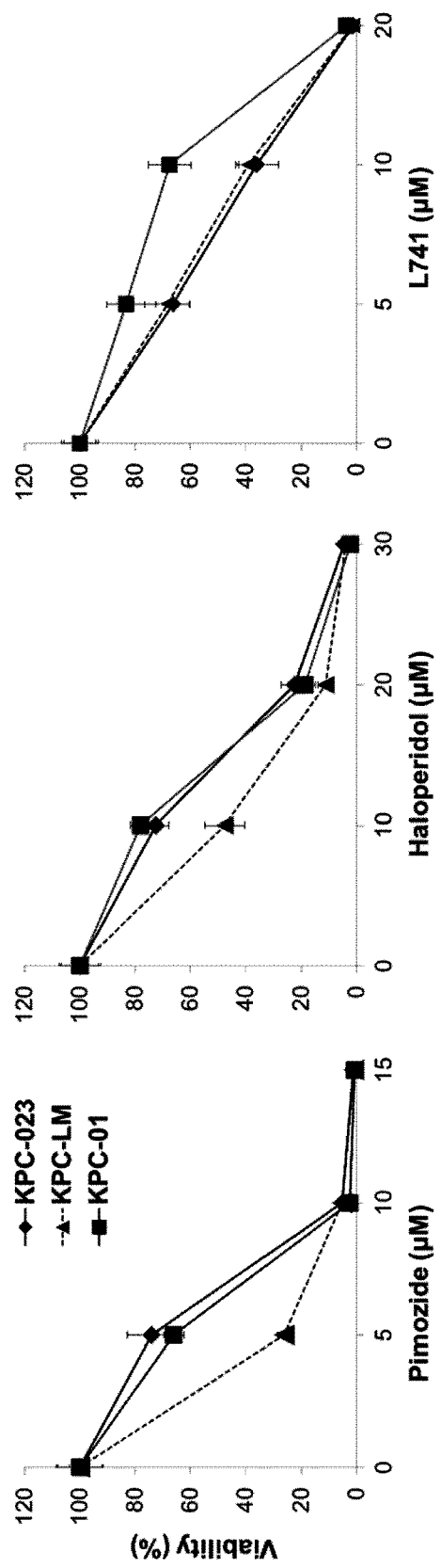

Pharmacological inhibition of DRD2 hampered tumor growth and metastasis in vivo as depicted in FIG. 9A. Notably, the data showed that primary and metastatic cancer cell lines isolated from a genetically engineered mouse model of PDAC were sensitive to DRD2 antagonists pimozide, haloperidol and L-741 demonstrated in FIG. 9B.

It has been reported that ER stress triggers a gene regulatory program, which is characterized by overexpression of genes encoding enzymes involved in glycolysis and lipogenesis. Furthermore, metabolomic studies have confirmed elevated glucose uptake, and glycolytic activity as well as increased phospholipid turnover and cholesterol levels in cancer cells under ER-stress conditions. Notably, the ER-stress-driven glycolysis and alterations in cholesterol homeostasis have been linked to chemoresistance in cancer cells, and have been highlighted as potential therapeutic targets. Interestingly, treatment with antipsychotic drugs, such as pimozide or haloperidol, which induce ER-stress in PDAC cells, modulates cholesterol metabolism in the same manner as triggered by ER-stress, and renders cancer cells vulnerable to cholesterol synthesis inhibitors. Therefore, the potential therapeutic benefits of combination of DRD2 antagonists with inhibitors of cholesterol synthesis and glucose metabolism in PDAC were investigated.

Figures 10A, 10B, 10C:
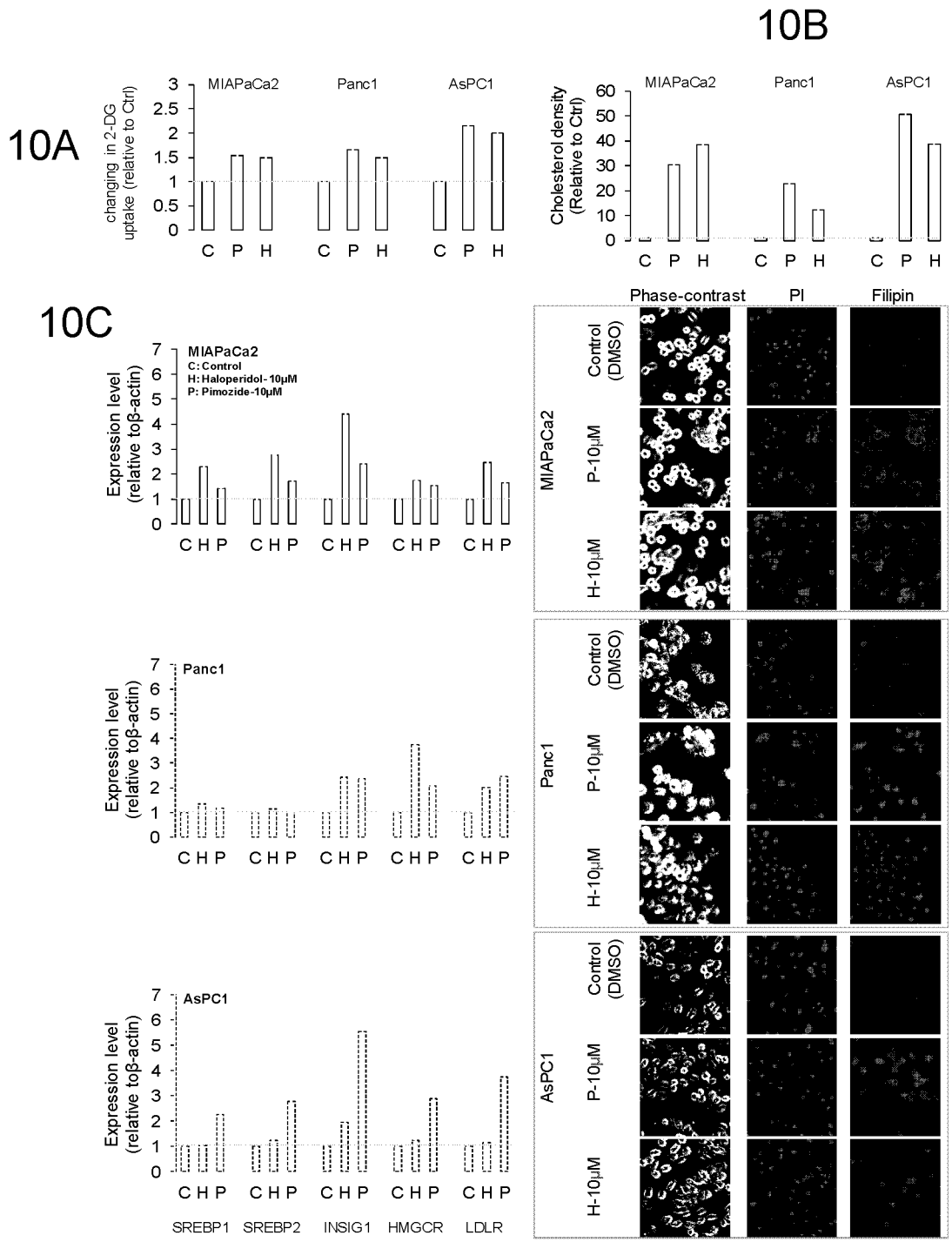
FIGS. 10A to 10C show an enhanced glucose and cholesterol uptake by pancreatic cancer cell lines following pimozide or haloperidol treatment. Measurement of 2-deoxy-D-glucose uptake shown on the y-axis relative to control by PDAC cell lines (MIAPaCa2, left; PANC-1, middle; AsPC1, right) treated with DMSO (C), pimozide (P) or haloperidol (H) (FIG. 10A). Abundance of free cholesterol, as measured by staining with filipin, after treatment with haloperidol (H) or pimozide (P) in PDAC cell lines (MIAPaCa2, left; PANC-1, middle; AsPC1, right) (FIG. 10B top). Representative micrographs of filipin-labelled cholesterol. PDAC (MIAPaCa2, top; PANC-1, middle; AsPC1, bottom) cells were seeded for 24 hours and treated with 10 μM haloperidol (H) or pimozide (P) or DMSO for 18 hours (FIG. 10B bottom). Red-fluorescence represents propidium iodide (PI)-stained nuclei and blue-fluorescence represents filipin-stained cholesterol. mRNA levels of genes relative to R-actin shown on the y-axis involved in cholesterol biosynthesis (from left to right: SREBP1, SREBP2, INSIG1, HMGCR, LDLR) measured by qRT-PCR 18 hours post-treatment with DMSO (C), haloperidol (H) or pimozide (P) in three PDAC cell lines (MIAPaCa2, top; PANC-1, middle; AsPC1, bottom) (FIG. 10C).

To verify that DRD2 antagonists affect glucose and cholesterol metabolism in PDAC cells, the effects of pimozide and haloperidol on glucose uptake, levels of free cholesterol and expression of cholesterol synthesis pathway were examined in three well-established PDAC cells lines: MIAPaCa-2, PANC-1 and AsPC-1. Treatment with pimozide or haloperidol resulted in an elevated uptake of glucose shown in FIG. 10A, in all three cell lines as evaluated by measuring the abundance of intracellular labelled 2-deoxy-D-glucose (2-DG), which was added to the cell culture media. Likewise, these treatments increased the abundance of free cholesterol in PDAC cells depicted in FIG. 10B, as measured through staining with Filipin, a fluorescent polyene antibiotic that binds to free (unesterified) cholesterol, while inducing expression of genes involved in lipogenesis as seen in FIG. 10C. These results showed that DRD2 antagonists increased glucose uptake and affected cholesterol homeostasis in PDAC cells.

Figures 11A, 11B:
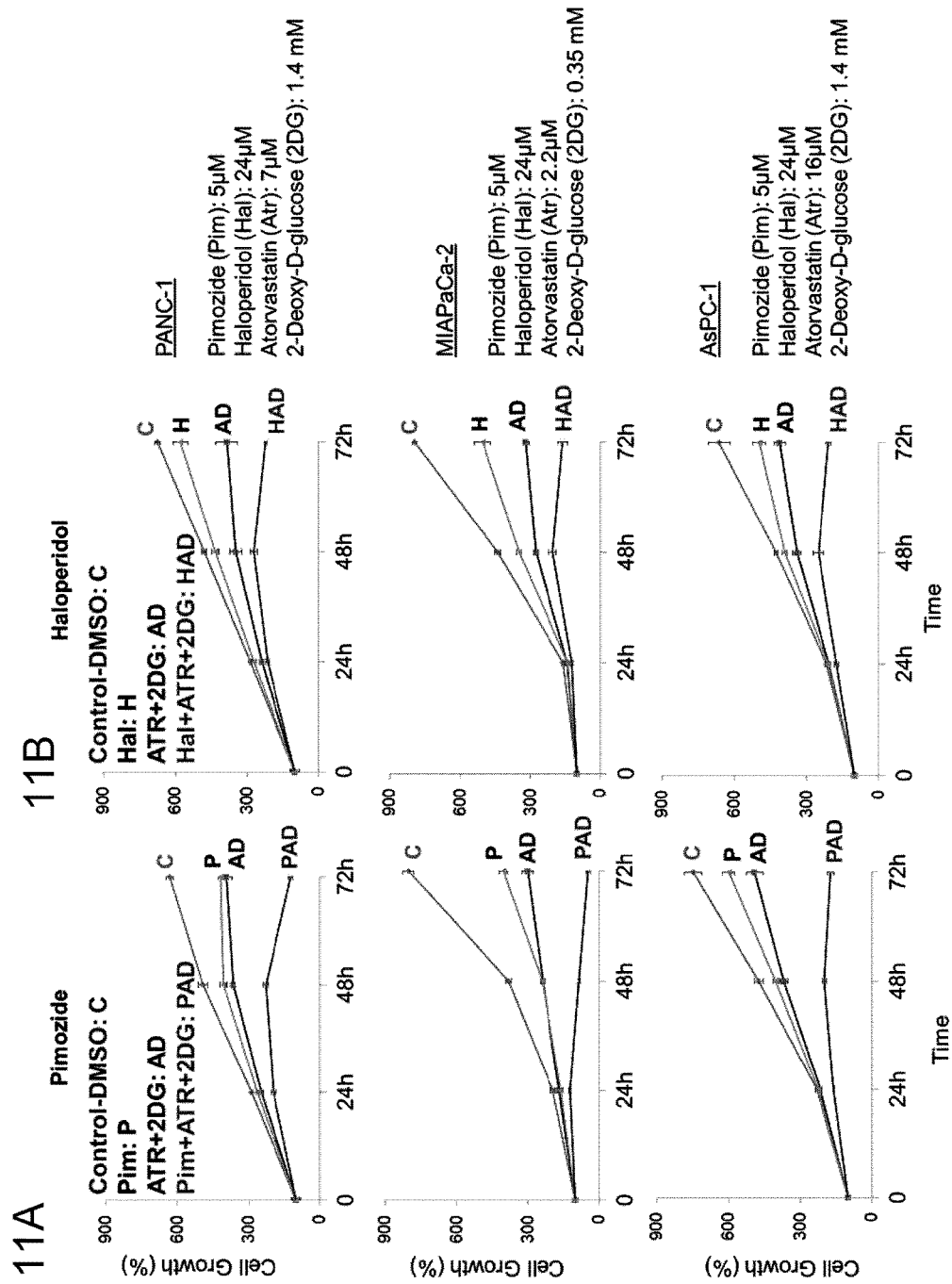
FIGS. 11A and 11B show PDAC cell line growth curves following combination therapy with DRD2 antagonists, 2-deoxy-D-glucose, and atorvastatin. Percentage cell growth shown on the y-axis following treatment with control (blue line), pimozide (Pim, gray line), atorvastatin and 2-deoxy-D-glucose (ATR+2-DG, red line) and combination of Pim and ATR+2-DG (green line) over time in PANC-1 (top), MIAPaCa-2 (middle) and AsPC-1 (bottom) cell lines (FIG. 11A). Haloperidol (Hal, gray line) is used as the DRD2 antagonist for use alone or in combination with ATR+2-DG as described in A (FIG. 11B). Dosage are indicated for each cell line.

PDAC cell proliferation was measured during pharmacological inhibition of DRD2 alone and in combination with blockade of glycolysis and cholesterol synthesis. To suppress glycolysis, 2-DG, a glucose analog which is a competitor inhibitor of glucose metabolism, was used. To inhibit cholesterol synthesis, atorvastatin (ATR), a competitive inhibitor of 3-hydroxy-3-methylglutaryl-coenzyme A (HMG-CoA) reductase in the cholesterol biosynthesis pathway was used. Treatment with 2-DG and ATR reduced cell growth in PDAC cell lines as did treatments with pimozide or haloperidol which is seen in FIGS. 11A and 11B. Notably, when combined with pimozide or haloperidol, the cocktail of 2-DG and ATR significantly potentiated anti-growth effects of DRD2 antagonists in a time-dependent manner as shown in FIGS. 11A and 11B. Without wishing to be bound to theory, these observations indicated that glycolysis and cholesterol biosynthesis pathways, which are activated by DRD2 antagonists, are used by cancer cells to survive the excessive ER stress induced by DRD2 antagonists.

The efficacy of the combined treatment approach was investigated using a MIAPaCa-2 xenograft model of pancreatic cancer. Since gemcitabine is the standard of care for pancreatic cancer, gemcitabine was included in the treatment regimen (Table 2).

TABLE 2

Trial designed to study effects of drugs and combination with gemcitabine

| Treatment group | Drug (dose) daily | Gemcitabine (20 mg/kg) every 4 days |
|---|---|---|
| 1 | Vehicle/DMSO | – |
| 2 | Pimozide (10 mg/kg) | – |
| 3 | ATR (5 mg/kg) 2-DG (400 mg/kg) | – |
| 4 | ATR (5 mg/kg) 2-DG (400 mg/kg) Pimozide (10 mg/kg) | – |
| 5 | Vehicle/DMSO | + |
| 6 | Pimozide (10 mg/kg) | + |
| 7 | ATR (5 mg/kg) 2-DG (400 mg/kg) | + |
| 8 | ATR (5 mg/kg) 2-DG (400 mg/kg) Pimozide (10 mg/kg) | + |

Figure 12C:
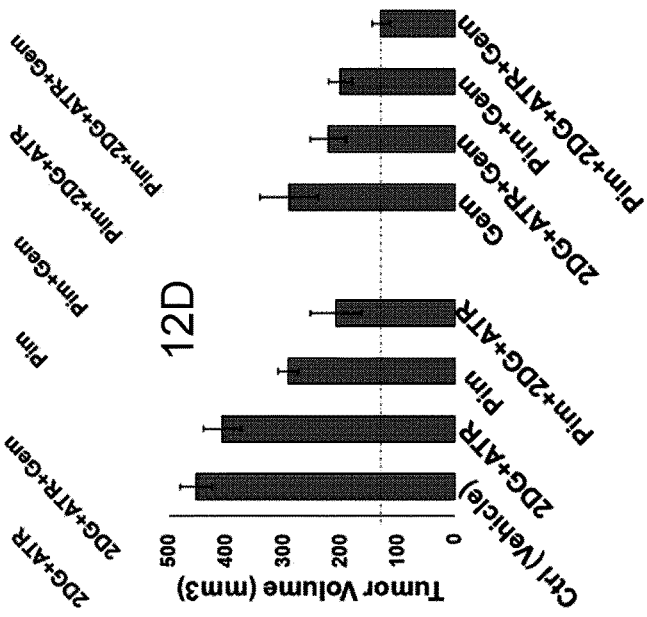
Figure 12D:
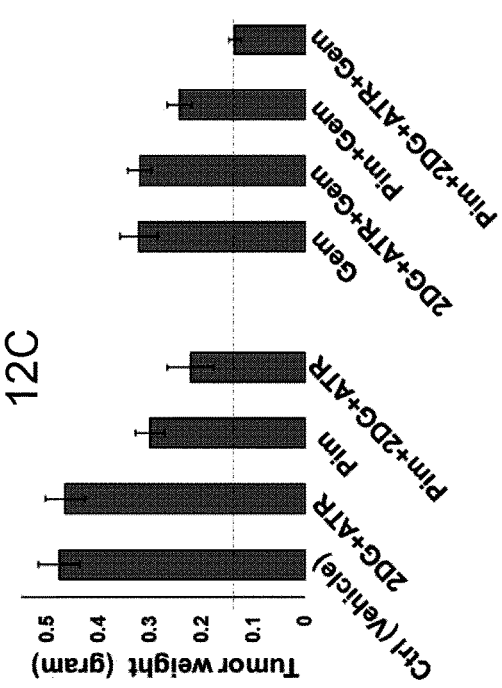

Gemcitabine reduced tumor weight and volume. Likewise, pimozide reduced tumor weight and volume. Combined together, these drugs resulted in a greater reduction of tumor size as depicted in FIGS. 12A, 12B, and 12C. In the absence of pimozide or gemcitabine, 2-DG and ATR did not reduce tumor growth. Moreover, these drugs also did not enhance the effect of gemcitabine versus gemcitabine alone. Consistent with the in vitro data, however, they did synergize with pimozide to enhance its effect on reducing cell tumor growth which can be seen in FIGS. 12A and 12B. Finally, the impact of a combined therapeutic approach for pimozide, gemcitabine, 2-DG and ATR resulted in complete arrest of tumor growth as shown in FIGS. 12A, 12B, and 12C.

The invention claimed is:

1. A method for the treatment of pancreatic cancer or pancreatitis in a subject in need thereof, the method comprises administering a therapeutically effective amount of a dopamine receptor antagonist, 2-deoxy-D-glucose (2-DG), and atorvastatin or a pharmaceutically acceptable salt thereof to the subject in need thereof, wherein the dopamine receptor antagonist is pimozide, haloperidol, or L-741,626.

2. The method of claim 1, further comprising administering a therapeutically effective amount of gemcitabine.

3. The method of claim 2, wherein gemcitabine is in dosages between 0.5 to 2 $g/m^2$ of body weight of the subject/week.

4. The method of claim 1, wherein the dopamine receptor antagonist is pimozide.

5. The method of claim 1, wherein the pancreatic cancer is a pancreatic ductal adenocarcinoma (PDAC).

6. The method of claim 1, wherein the pancreatitis is a chronic pancreatitis.

7. The method of claim 1, wherein the subject is a human.

8. The method of claim 1, wherein the dopamine receptor antagonist, 2-DG, and atorvastatin or a pharmaceutically acceptable salt thereof are administered daily.

9. The method of claim 1, wherein the dopamine receptor antagonist is administered in dosages between 0.05 to 0.5 mg/kg of body weight of the subject/day.

10. The method of claim 1, wherein 2-DG is administered in dosages between 5 to 500 mg/kg of body weight of the subject/week.

11. The method of claim 1, wherein atorvastatin or the pharmaceutically acceptable salt thereof is in dosages between 1 to 250 mg/day.

\* \* \* \* \*